(12) United States Patent
Kakefuda et al.

(10) Patent No.: US 7,285,701 B2
(45) Date of Patent: Oct. 23, 2007

(54) CYANOBACTERIAL NUCLEIC ACID FRAGMENTS ENCODING PROTEINS USEFUL FOR CONTROLLING PLANT TRAITS VIA NUCLEAR OR PLASTOME TRANSFORMATION

(75) Inventors: Genichi Kakefuda, Chapel Hill, NC (US); Rui-Guang Zhen, Chapel Hill, NC (US)

(73) Assignee: BASF Plant Science GmbH NC (US)

( * ) Notice: Subject to any disclaimer, the term of this patent is extended or adjusted under 35 U.S.C. 154(b) by 36 days.

(21) Appl. No.: 11/244,732

(22) Filed: Oct. 6, 2005

(65) Prior Publication Data

US 2006/0143730 A1    Jun. 29, 2006

Related U.S. Application Data

(62) Division of application No. 09/893,033, filed on Jun. 27, 2001, now Pat. No. 7,083,967.

(51) Int. Cl.
*A01H 1/00*   (2006.01)
*C12N 9/00*   (2006.01)
*C12N 15/00*  (2006.01)

(52) U.S. Cl. .................. 800/278; 435/183; 435/189; 435/152.3; 435/320.1; 435/410; 435/468; 536/23.2

(58) Field of Classification Search ............... 800/278; 435/183, 189, 252.3, 320.1, 410, 468; 536/23.2
See application file for complete search history.

(56) References Cited

OTHER PUBLICATIONS

Windhovel, U., et al., "Engineering Cyanobacterial Models Resistant to Bleaching Herbicides", Pestic. Biochem. Physiol., 1994, 49: 63-71.

Sandmann, G., et al., "Phytoene Desaturase, the Essential Target for Bleaching Herbicides", Weed science, 1991, 39:474-479.

Windhovel, U., et al.,"Expression of Erwinia uredovora Phytoene Desaturase in Synechococcus PCC7942 Leading to Resistance against . . . ", Plant Physiol., 1994, 104:119-125.

Linden,H., et al., "Biochemical Characterization of Synechococcus Mutants Selected against the Bleaching Herbicide Norflurazon", Pestic.Biochem.Physiol.,1990,36:46-51.

Chamovitz,D., et al., "The molecular basis of resistance to the herbicide norflurazon", Plant Mol. Biol., 1991, 16:967-974.

Martinez-Ferez,I.M.,et al., "Nucleotide sequence of the phytoene desaturase gene from Synechocystis sp. PCC6803 and characterization . . . "Plant Mol.Biol.,1992,18:981-983.

Martinez-Ferez,I.,et al.,"Mutagenesis of an Amino Acid Responsible in Phytoene Desaturase from Synechocystis for Binding . . . ", Pestic.Biochem.Physiol.,1994,48:185-190.

Synechocystis sp. pds gene for phytoene desaturase X62574. Plant Mol. Biol. 18(5), 981-983 (1992).

*Primary Examiner*—Tekchand Saidha
(74) *Attorney, Agent, or Firm*—Ruoying Chen

(57) ABSTRACT

This invention provides cyanobacteria as an alternative source of ahas and pds genes for plant transformations and for selectable markers. In particular, it provides for cyanobacteria, for example, *Synechocystis*, as a source of genes encoding herbicide insensitive proteins, and elements of genes for control of expression in plastids. Nucleic acid fragments, both the acetolactate synthase (ahas) large subunit and the ahas small subunit, were found to provide herbicide resistance. Also, the present invention provides novel *Synechocystis* mutant phytoene desaturase (PDS) gene conferring resistance to 4'-fluoro-6[(alpha,alpha,alpha,-trifluoro-m-tolyl)oxy]-picolinamide, a bleaching herbicide. The present invention provides improvements to method involving cyanobacteria for the screening of compounds, including a new high-through-put protocol that is a rapid and cost effective way to identify target site genes.

7 Claims, 15 Drawing Sheets

Figure 2A:
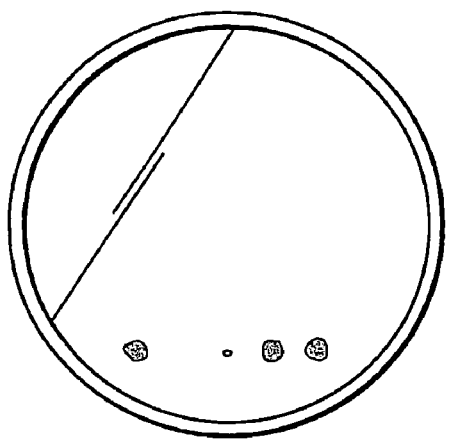
Figure 2B:
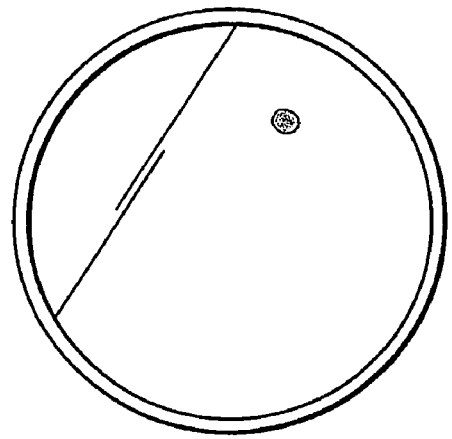
Figure 2C:
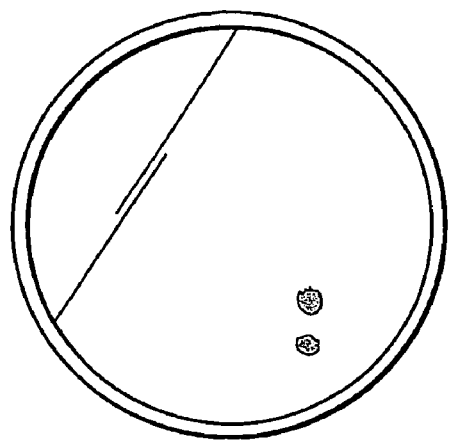
Figure 2D:
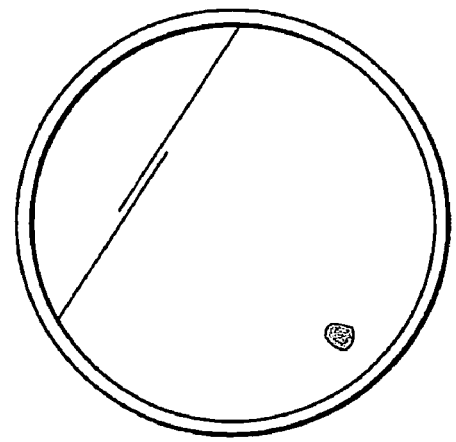

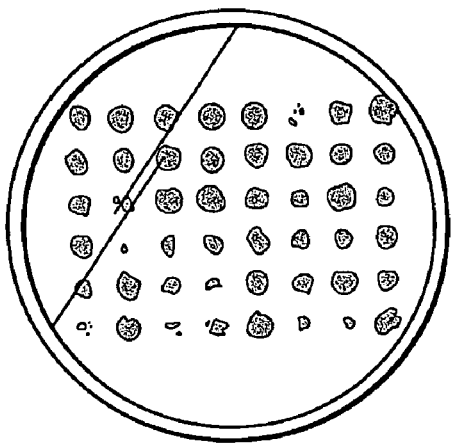
FIG. 1A
CONCENTRATION OF
4'-FLOURO-6-[(ALPHA,ALPHA,ALPHA,
-TRIFLOURO-M-TOLYL)OXY]-
PICOLINAMIDE: 0
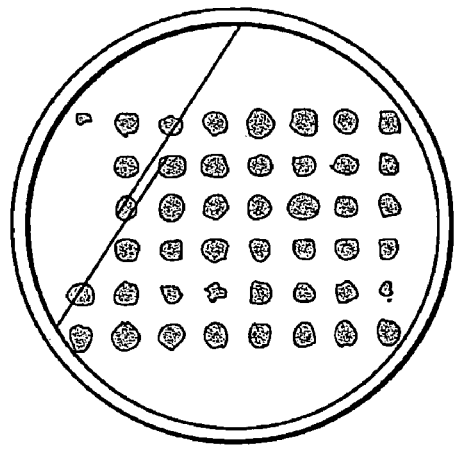
FIG. 1B
CONCENTRATION OF
4'-FLOURO-6-[(ALPHA,ALPHA,ALPHA,
-TRIFLOURO-M-TOLYL)OXY]-
PICOLINAMIDE: 2 µM
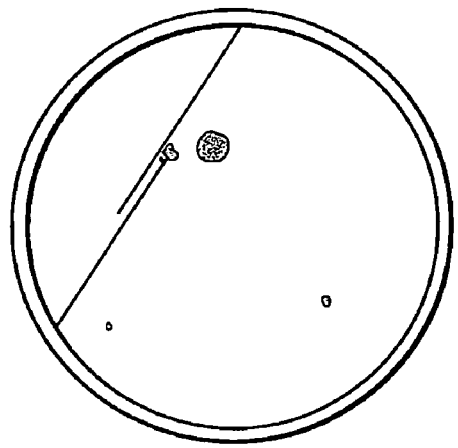
CONCENTRATION OF
4'-FLOURO-6-[(ALPHA,ALPHA,ALPHA,
-TRIFLOURO-M-TOLYL)OXY]-
PICOLINAMIDE: 5 µM

EXPERIMENT V, PLATE #1

EXPERIMENT VII, PLATE #2

EXPERIMENT VII, PLATE #3

EXPERIMENT VII, PLATE #4

WILD TYPE 5-1/12E 5-1/12F 7-2/1E 7-3/11F 7-3/12E 7-4/12F ptions, and
elements of genes for control of expression in plastids.

CYANOBACTERIAL NUCLEIC ACID FRAGMENTS ENCODING PROTEINS USEFUL FOR CONTROLLING PLANT TRAITS VIA NUCLEAR OR PLASTOME TRANSFORMATION

CROSS REFERENCE TO RELATED APPLICATIONS

This application is a divisional application of U.S. Nonprovisional patent application Ser. No. 09/893,033 filed Jun. 27, 2001, now U.S. Pat. No. 7,083,967, and claims the priority benefit of U.S. Provisional Application Ser. No. 60/214,705 filed Jun. 27, 2000, both of which are hereby incorporated in their entirety.

FIELD OF THE INVENTION

The present invention relates to improved screening methods for identifying and utilizing cyanobacterial genes for modifying plant traits, and to cyanobacteria as an alternative source of ahas and pds genes for plant transformations, in particular genes encoding herbicide insensitive proteins, and elements of genes for control of expression in plastids.

BACKGROUND OF THE INVENTION

Cyanobacteria are considered to be the precursor of plant chloroplasts. Cyanobacteria possess all beneficial features of prokaryotes like ease of handling, rapid growth under defined conditions, availability of replica plating techniques, easy genetic manipulation by mutagenesis or transformation and availability of established mutants. Cyanobacteria also share important features with higher plant metabolism such as oxygenic photosynthesis by two photosystems and autotrophy with respect to reduced nitrogen, sulfur and carbon dioxide. Therefore, efficacy of compounds in cyanobacteria can be indicative of similar performance in higher plants.

The photosynthetic membranes of cyanobacteria, plants and algae contain essential pigments called carotenoids, which function in protecting chlorophyll against photo oxidative damage by singlet oxygen, as well as acting as accessory pigments in photosynthetic light harvesting. These carotenoids are also precursors of vitamin A in human and abscissic acid in plants. The first committed step in carotenoids biosynthesis is the condensation of two molecules of geranylgeranyl pyrophosphate (GGPP) to yield the colorless phytoene. Desaturation of phytoene through the insertion of four double bonds gives rise to lycopene, and further cyclization reactions lead to the generation of β-carotene. Phytoene desaturase(pds) mediates the first two steps of desaturation of phytoene, disruption of which results in an observable bleaching symptom. As such, a number of commercial herbicides directed at inhibiting this enzyme have been developed, e.g. norflurazon, fluridone, and fluorochloridone.

In addition, as ancestral precursors to chloroplasts, cyanobacterial genes share features common to chloroplast genes. Gene elements, such as promoters, ribosome binding sites, etc. are similar and can be cross-functional between chloroplast and cyanobacteria. Therefore cyanobacterial genes make ideal candidates for plastome targeted transformation, and in particular chloroplast transformation.

There are a number of references in the literature to screening methods and assays utilizing cyanobacteria. These include methods using cyanobacteria for the screening of compounds to identify inhibitors of specific metabolic pathways and to identify novel herbicidal modes of action. [Windhovel et al, 1994, and 1997] describes an *Erwinia* gene transformed into host cells selected of cyanobacteria specifically *Synechococcus* PCC 7942 and *Synechocystis* PCC 6803, which was used as a screen for beta-carotene biosynthesis and for mutants resistant to herbicides specifically bleaching herbicides of the trialkylamine family. The screening for bleaching activity is described by [Sandmann et al, 1991] as a means to discover new herbicides with different core structures which inhibit phytoene desaturase (pds), a membrane bound enzyme in the carotenogenic pathway catalyzing the hydrogen abstraction step at the first C40 precursor of beta-carotene. [Windhoevel et al, 1994] describes a screen involving genes coding for pds of the non-photosynthetic bacterium *Erwinia uredovora* introduced into the cyanobacterium *Synechococcus* as a convenient experimental model for higher plant transformation and resistance to herbicides. The functionality of the heterologously expressed phytoene desaturase in the transformants was demonstrated in assays. Other references such as [Babczinski et al, 1995] identify a new class of pds inhibiting herbicides based on a screen utilizing the unicellular cyanobacteria *Anacystis*. [Chamowitz et al, 1993] describes a cell-free carotegenic assay to identify herbicide resistant algal pds mutants. Inhibition of carotenoid biosynthesis by herbicidal m-phenoxybenzamide derivatives was investigated in a cell-free in vitro assay using the cyanobacteria *Aphanocapsa* by [Clarke et al, 1985], and subsequently by [Kowalczyk-Schroeder et al, 1992]. [Sandmann et al, 1996] describes a non-radioactive cell-free assay to quantitatively determine inhibition of plant-type pds by bleaching herbicides. They further developed a cyanobacterial pds assay system, a mode of action assay utilizing the cyanobacteria *Anacystis*, and assays using algal cells. The present invention, however, differs by identifying improvements to the current screening methods and assays, and uses these improvements to identify novel nucleic acid fragments having herbicide resistant mutations in the pds gene.

The prokaryotic acetolactate synthase (ahas) enzyme exist as two distinct, but physically associated protein subunits. In prokaryotes, the two polypeptides, a "large subunit" and a "small subunit", are expressed from separate genes. Three major ahas enzymes, designated I, II, III, all having large and small subunits have been identified in enteric bacteria. In prokaryotes, the ahas enzyme has been shown to be a regulatory enzyme in the branched amino acid biosynthetic pathway [Miflin et al, 1971], and only the large subunit has been observed as having catalytic activity. From studies of ahas enzymes from microbial systems, two roles have been described for the small subunit: 1) the small subunit is involved in the allosteric feedback inhibition of the catalytic large subunit when in the presence of isoleucine, leucine or valine or combinations thereof; and 2) the small subunit enhances the activity of the large subunit in the absence of isoleucine, leucine or valine. The small subunit has also been shown to increase the stability of the active conformation of the large subunit. The expression of the small subunit can also increase the expression of the large subunit as seen for AHAS I from *E. coli* [Weinstock et al., 1992].

The ahas large subunit protein has been identified in plants, and has also been isolated and used to transform plants. An ahas mutant allele isotype of the ahas III large subunit protein, having the tryptophan at position 557 replaced with leucine has been found in a *Brassica napus* cell line [Hattori et al., 1995]. The mutant protein product of this gene confers sulfonylurea, imidazolinone and triazolopyridine resistance to the cell line. This mutant allele, when expressed in transgenic plants, also confers resistance to these herbicides.

Until recently, there was no direct evidence that a small subunit protein of ahas existed in eukaryotic organisms. Recently, other groups, through the use of Expressed Sequence Tags (ESTs), have identified sequences homologous to the microbial ahas small subunit genes in a eukaryote, the plant *Arabidopsis*. These groups showed that a randomly isolated *Arabidopsis* cDNA sequence had sequence homology with the ahas small subunit sequences from microbial systems. Since then, ESTs from small subunit genes have been described from other eukaryotes such as yeast and red algae. [Duggleby et al, 1997] describes three EST sequences, two from *Arabidopsis* and one from rice, that have homology to known prokaryotic small subunit cDNA sequences from *P. purpurea*.

Several references to ahas screens and assays utilizing cyanobacteria exist in the prior art. [Powell et al, 1990], reported on the role of cyanobacteria for herbicide screening but no mention was made of the ahas "small subunit" identified in our invention. They reported that our understanding of the mode of action of certain herbicides which inhibit photosynthesis has been facilitated by studies with cyanobacteria. In the case of sulfonylurea herbicides which inhibit branched chain amino acid biosynthesis, the resistance shown by a cyanobacterium is due to an insensitive acetolactate synthase enzyme. These studies are not consistent with the results reported by Freiburg et al. 1990 discussed below, in which the cyanobacterial gene is sensitive. If other insensitive target enzymes were to be found, cyanobacteria could be useful sources of genes for the cloning of herbicide resistance into higher plants. They presented data showing high levels of resistance of certain cyanobacteria to glyphosate, an inhibitor of aromatic amino acid biosynthesis. [Dunahay et al, 1997] discloses a method to transform chlorophyll containing algae, which includes introducing a recombinant molecule comprising a nucleic acid molecule encoding a dominant selectable marker operatively linked to an algal regulatory control sequence into the chlorophyll C-containing algae. However, unlike our invention, the mutant ahas was introduced into algae, not cyanophycae, to detect inhibitors.

WO98/06862 (Calgene) discloses plants transformed with the *Erwinia* phytoene desaturase gene for altered carotenoid levels and fatty acid. JP 6,343,476 (Kirin Brewery) describes the production of bleaching herbicide-resistant plants by transformation with the *Erwinia* pds gene. WO 98/20144 (Zeneca) discloses transgenic plants resistant to many classes of herbicides but the source of the genes, whether pds or ahas or from *Synechocystis* is unspecified. Also, U.S. Pat. No. 5,378,824 (Dupont) and U.S. Pat. No. 5,661,017 (Dunahay et al.) both report the transformation of a plant ahas gene, not a *Synechocystis* gene, into a number of phyla and classes including algae.

Freiburg et al, 1990, reported on herbicide resistant *Synechococcus* ahas gene expressed in *E. coli*. The report describes the isolation and molecular characterization of *acetolactate synthase* genes from the sulfonylurea-sensitive enzyme and from the sulfonylurea-resistant mutant, which specifies the enzyme resistant to sulfonylurea herbicides. The ALS gene was cloned and mapped by complementation of an *E. coli* ilv auxotroph that requires branched-chain amino acids for growth and lacks ALS activity. The cyanobacterial gene is efficiently expressed in this heterologous host. The resisitant phenotype is a consequence of proline to serine substitution in residue 114 of the deduced aminoacid sequence. Functional expression of the mutant gene in *Synechococcus* and in *E. coli* confirmed that this amino acid sequence is responsible for the resistance. [Linden et al, 1990], reported cyanobacteria *Synechococcus* PCC 7942 mutants selected against the bleaching herbicide norflurazon. One strain exhibited cross-resistance against another bleaching herbicide fluorochloridone, but the other three strains did not show cross-resistance against other phytoene desaturase (pds) inhibitors. Further, [Linden et al, 1991] reported on mutants from *Synechococcus* PCC 7942, which were selected for tolerance to various bleaching herbicides. A mutant NFZ4 established a high degree of cross-resistance to both norflurazon and fluorochloridone but not to fluridone. [Chamowitz et al, 1991] cloned and sequenced a pds gene from the cyanobacteria *Synechococcus* PCC 7942, also resistant to the bleaching herbicide norflurazon. The identified mutant is a Val→Gly change at position 403 in the *Synechococcus*, but not *Synechocystis* pds protein. [Sandmann and Fraser 1993] reported bacterial and fungal pds as a target for bleaching herbicides, and discussed the identification of cyanobacterial mutants with resistance to specific compounds and their cross-resistance to other bleaching herbicides.

Cyanobacteria *Synechocystis* was originally described in Martinez-Ferez and Vioque 1992. A spontaneous mutant, strain AV4, which is resistant to norflurazon, was isolated from *Synecchocystis* PC 6803. DNA isolated from the mutant AV4 can transform wild-type cells to norflurazon resistance with high frequency. Sequence analysis of the clone identified an open reading frame that is highly homologous to the previously sequenced pds genes from *Synechococcus* and soybean. In both cyanobacteria and plants the pds gene is highly conserved: the *Synecchocystis* PCC 6803 pds gene is 82% and 61% identical to the *Synechococcus* PCC 7942 and the soybean pds genes respectively. [Martinez-Ferez et al, 1994] identified three distinct *Synechocystis* mutants selected against norflurazon, and showed modification of the same amino-acid of phytoene desaturase into three different ones. In all cases, the same amino-acid Arg$^{195}$ was modified either into Cys, Pro or Ser. The degree of resistance was highest when Arg was changed into Ser.

While the literature has several references to pds herbicide resistant transgenic plants, our invention exemplifies improvements to current cyanobacteria screening methods. Our improvement has identified novel nucleic acid fragments from *Synechocystis* PCC 6803. The mutant pds (phytoene desaturase) gene and ahas large and small subunits are useful in the identification of novel pds and ahas inhibitors and, in plant transformations for conferring resistance and cross-resistance to certain bleaching herbicides and AHAS-inhibiting herbicides.

SUMMARY OF THE INVENTION

Therefore, the present invention improves the current cyanobacteria screening methods. Our improvement has, in turn, identified novel nucleic acid fragments from the cyanobacterial *Synechocystis* PCC6803. The mutant pds (phytoene desaturase) gene and ahas (Acetohydroxyacid synthase) large and small subunits are useful in the identification of novel pds and ahas inhibitors and, in plant transformations for conferring resistance and cross-resistance to certain bleaching herbicides and imidazolinones.

Specifically, screening methods were used for identification of novel *Synechocystis* mutations that provide resistance to 4'fluoro-6-[(alpha,alpha,alpha,-trifluoro-m-tolyl)oxy]-picolinamide, an inhibitor of pds.

The identification of a novel mutation in the pds gene together with the fact that this gene is highly homologous between cyanobacteria and plants, will aid our efforts in engineering crops for resistance to herbicides through the introduction of site-directed mutation in the target pds gene.

Novel mutations displaying unique resistance to 4'-fluoro-6[(alpha,alpha,alpha,-trifluoro-m-tolyl)oxy]-picolinamide will aid in programs of engineering crops for resistance to 4'-fluoro-6-[(alpha,alpha,alpha,-trifluoro-mtolyl)oxy]-picolinamide and potentially other pds inhibiting herbicides via chloroplast-mediated transformation. Alternatively, mutant forms of pds genes with mutation(s) at position(s) similar to the *Synechocystis* gene can be obtained for any given crop species, and used further for genetic transformation. The identification of additional novel mutations conferring resistance to 4'-fluoro-6-[(alpha,alpha,alpha,-trifluoro-m-toly)oxy]-picolinamide should shed light on the structure of 4'-fluoro-6-[(alpha,alpha,alpha,-trifluoro-m-toly)oxy]-picolinamide binding site, and serve as a valuable guide for designing novel inhibitors of this enzyme.

Therefore, in preferred embodiments, the present invention provides novel *Synechocystis* mutant pds gene(s) conferring resistance to 4'-fluoro-6-[(alpha,alpha,alpha,-trifluoro-m-toly)oxy]-picolinamide.

Also, in further preferred embodiments, the present invention provides a method of using a simple genetic system, *Synechocystis*, to select and isolate mutants forms resistant to 4'-fluoro-6-[(alpha,alpha,alpha,-trifluoro-m-toly)oxy]-picolinamide.

In additional embodiments, a method for the preparation of pds resistant nucleic acid fragments from the cyanobacteria *Synechocystis* EMS resistant cell lines is provided.

In additional preferred embodiments, the present invention provides novel *Synechocystis* mutant pds gene(s) conferring cross-resistance to known PDS inhibitors and 4'-fluoro-6-[(alpha,alpha,alpha,-trifluoro-m-toly)oxy]-picolinamide.

Another approach to the use of cyanobacterial genes for controlling plant traits is to use natural cyanobacterial genes, which already have desired characteristics. The acetolactate synthase (AHAS) enzymes from *Synechocystis* PCC6803 and *Anabaena* PCC7120 are naturally resistant to imidazolinone and other AHAS inhibiting enzymes. The AHAS genes from these cyanobacteria could therefore be used to transform crop species thereby conferring herbicide resistance.

These cyanobacterial mutant genes, isolated from cyanobacterial sources, can be useful not only for herbicide resistance but also as selectable markers for herbicide, fungicide and insecticide resistance genes as well as output trait genes, as a component for a selection system when coupled with the imidazolinones and other herbicides. Such a selectable marker system for nuclear or plastidic transformation could be used for major monocot and dicot crops such as maize, wheat, barley, canola, rice, tobacco, and soybean.

Thus, the present invention provides for improvements to current methods for identifying and utilizing cyanobacterial genes for modifying plant traits including herbicide resistance. Improvements include methods for screening of compounds to identify novel herbicidal modes of action and identify novel herbicide resistant mutations.

Thus, in preferred embodiments, the present invention provides a nucleic acid fragment encoding a herbicide resistant acetolactate synthase (ahas) large subunit gene from the cyanobacterium *Synechocystis* PCC6803 and was cloned from a genomic DNA library.

In further preferred embodiments, a nucleic acid fragment encoding a herbicide resistant acetolactate synthase (ahas) small subunit gene from the cyanobacterium *Synechocystis* PCC6803 was cloned from a genomic DNA library.

In additional preferred embodiments, this invention provides cyanobacteria as an alternative source of ahas and pds genes for plant transformations, in particular genes encoding herbicide insensitive proteins, and elements of genes for control of expression in plastids.

The present invention also provides a method for the improved genetic transformation of *Synechocystis*.

Finally the present invention provides for the use of the cyanobacterial pds and ahas genes as a selectable marker for transformations, and as a means of selection with the imidazolinones and 4'-fluoro-6-[(alpha,alpha,alpha,-trifluoro-m-toly)oxy]-picolinamide for herbicide resistance.

Additionally provided for is a method for target site gene identification, specifically, protocols for "High-Through-Put" molecular manipulation of cyanobacteria *Synechocystis*. This High-Through-Put system allows us to determine the mode of action of commercial and/or novel compounds for which the mode of action is unknown.

The integration of the processes, along with the described improvements of screening for *Synechocystis* mutants resistant to herbicides, the preparation of genomic DNA from the mutants, the transformation of *Synechocystis* of fragments of mutant DNA, and the identification of transformants which are conferred herbicide resistance from the DNA fragments, and the sequencing of the DNA fragment to identify the target of the herbicide, the mutation conferring herbicide resistance, combined provide for an improved method for identifying novel Mode of Action and mutations within genes for altered traits.

BRIEF DESCRIPTION OF THE FIGURES/DRAWINGS

Figure Legends

Figures 1, 3:
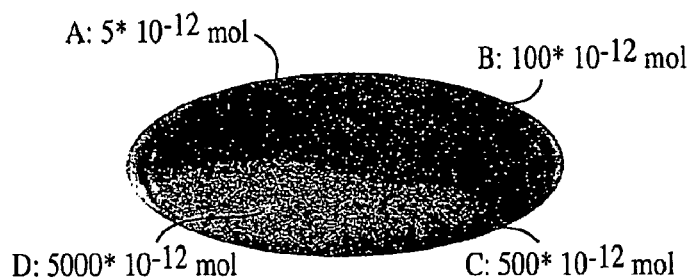

FIG. 1. Selection of true resistant mutants.

Figures 2, 3:
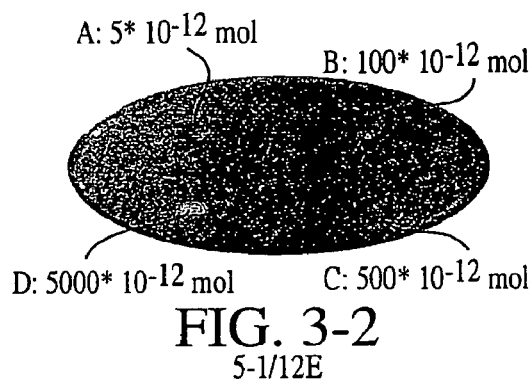
Figure 3:
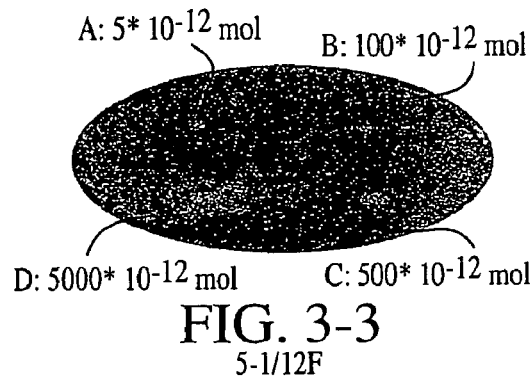

FIG. 2. Identification of *Synechocystis* resistance mutant. (Resistant colonies plated on 5 µM 4'-fluoro-6-[(alpha,alpha,alpha,-trifluoro-m-tolyl)oxy]-picolinamide plates).

FIG. 3. Susceptibility test of wild type and 4'-fluoro-6-[(alpha,alpha,alpha,-trifluoro-m-tolyl)oxy]-picolinamide, mutants of *Synechocystis* using the paper disc assay. (Inhibition of wild-type *Synechocystis* in paper disc assay).

Figures 3, 4:
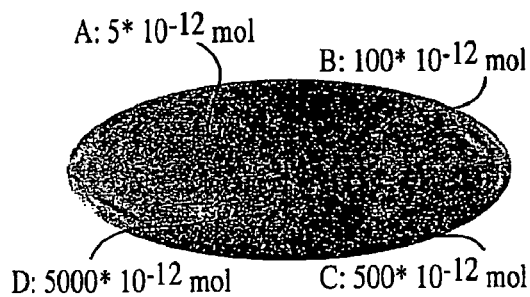

FIG. 4. Dose-response curve of *Synechocystis* wild type and 4'-fluoro-6-[(alpha,alpha,alpha,-trifluoro-m-tolyl)oxy]-picolinamide resistant mutants after seven days of suspension culture.

Figures 3, 4, 5:
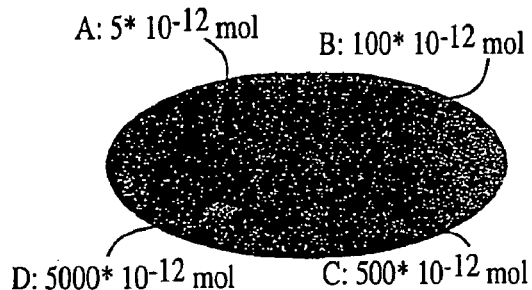

FIG. 5. HighThroughPut (HTP) Target Site Gene Identification in *Synechocystis*.

Figures 3, 4, 5, 6:
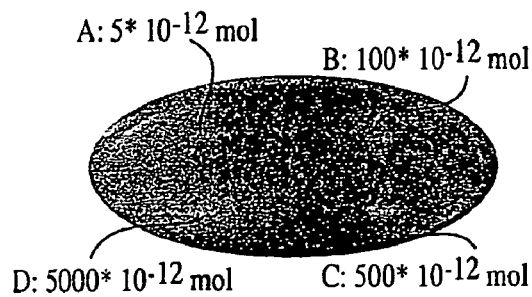

FIG. 6. In vivo growth of *Synechocystis* PCC 7120 and *Anabaena* PCC7120 cultured in BG-11 media in the presence of increasing concentrations of PURSUIT® imazethapyr and OUST® sulfometuron methyl.

Figures 3, 4, 5, 6, 7:
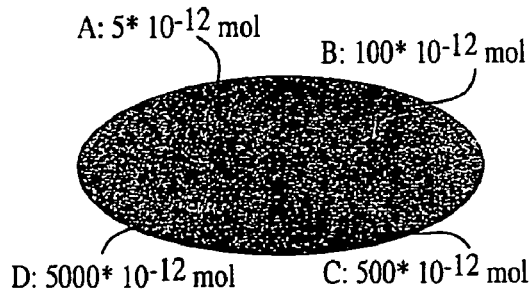
Figure 4:
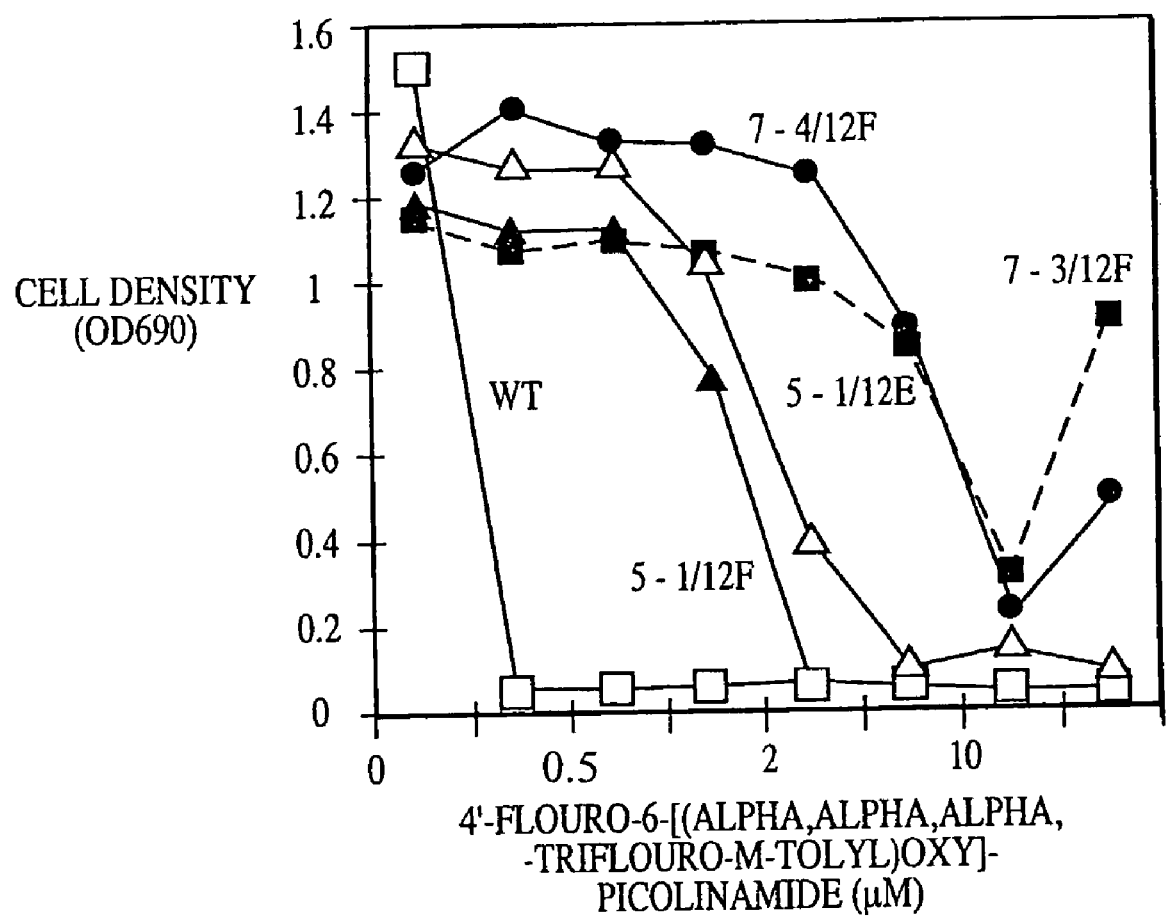
Figure 5:
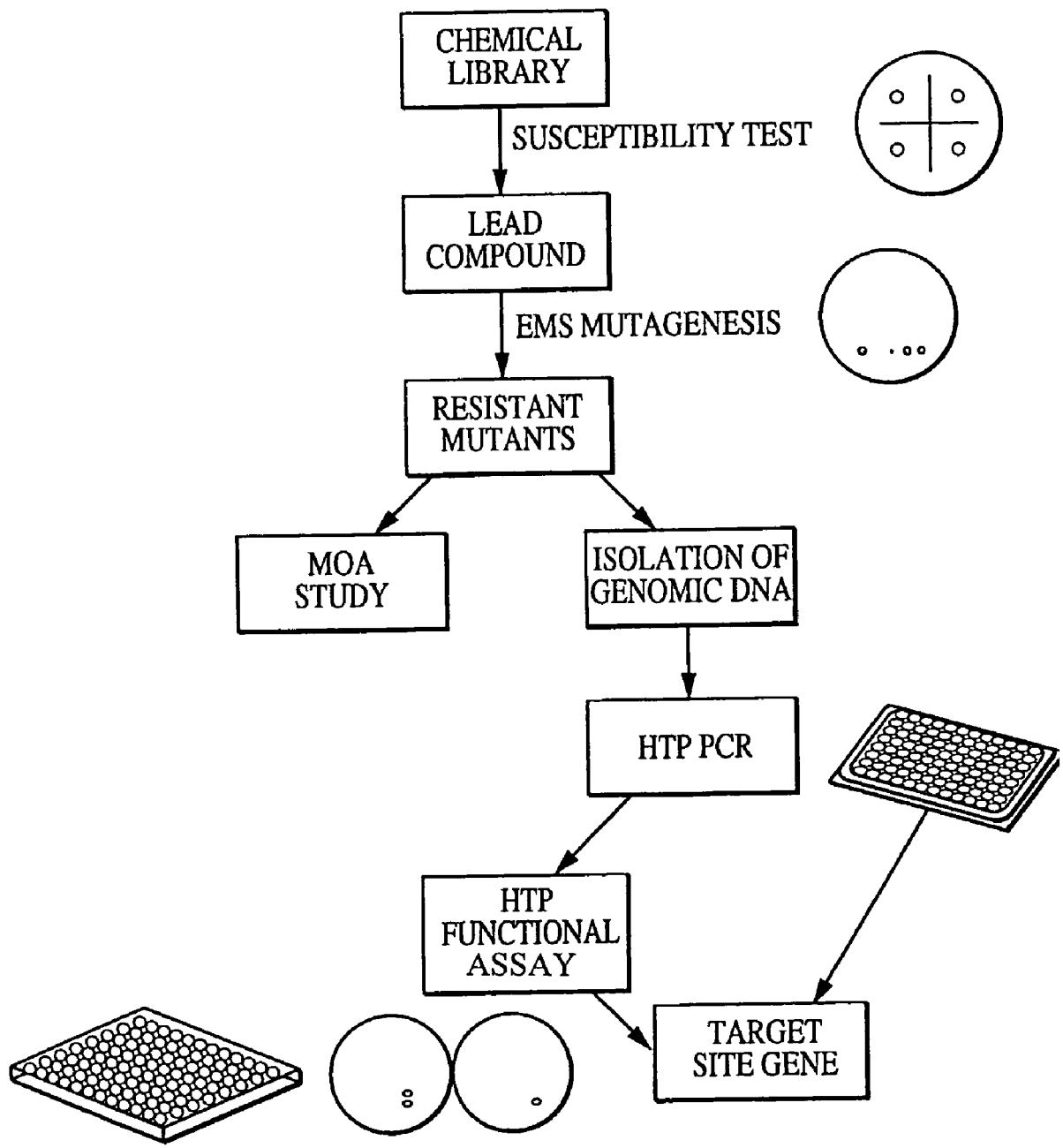
Figure 6:
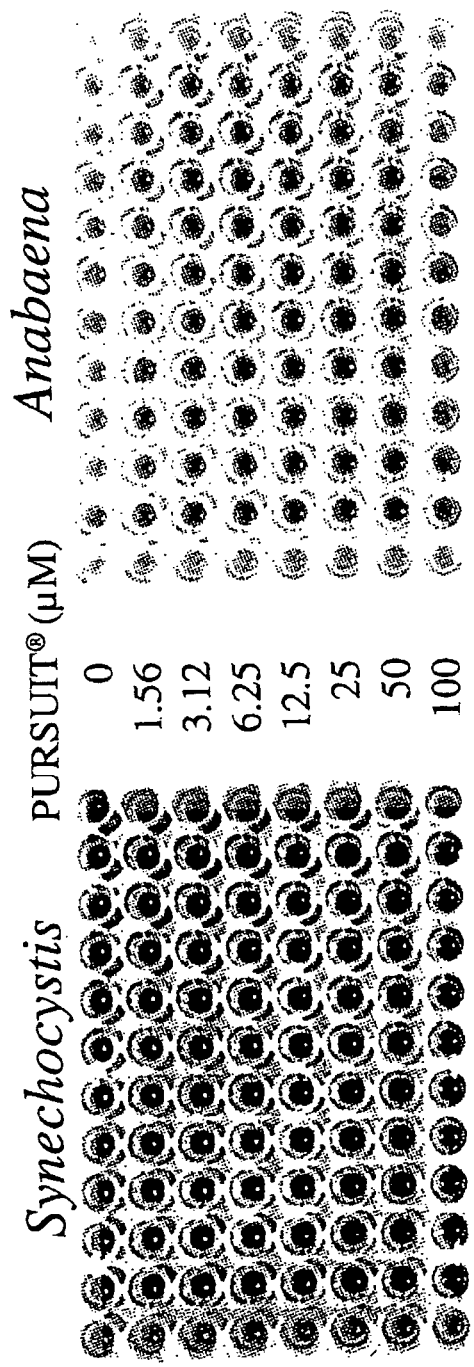
Figure 6:
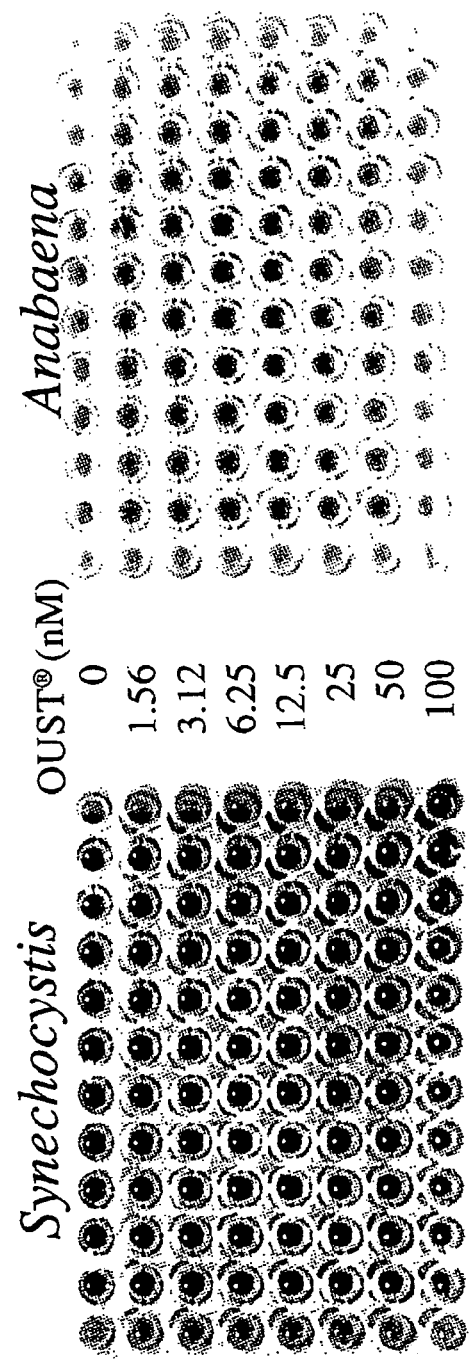
Figure 7:
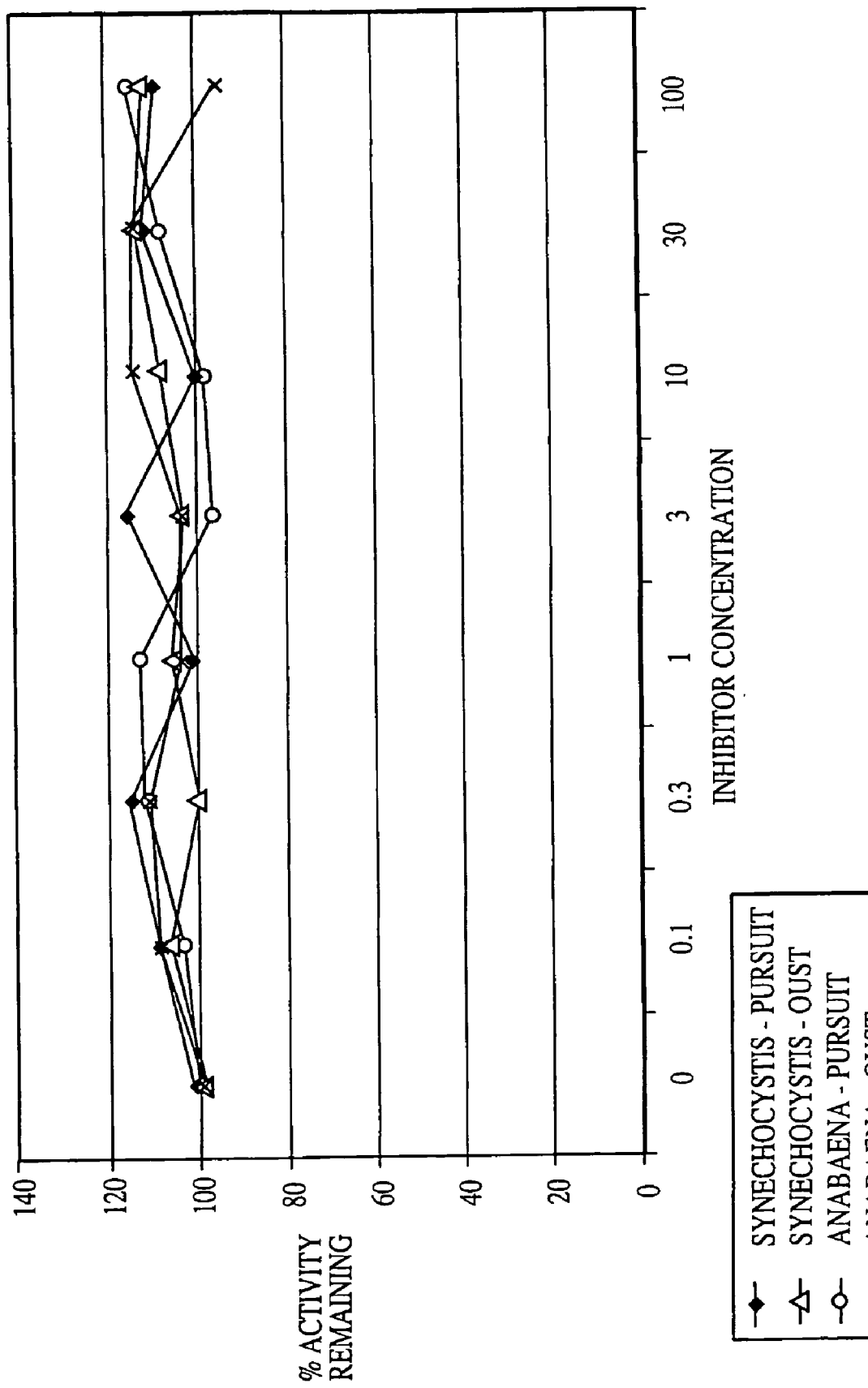

FIG. 7. In vitro activity of *Synechocystis* PCC 7120 and *Anabaena* PCC7120 AHAS with increasing concentrations of PURSUIT® imazethapyr and OUST® sulfometuron methyl.

Figure 8A:
Figure 8B:
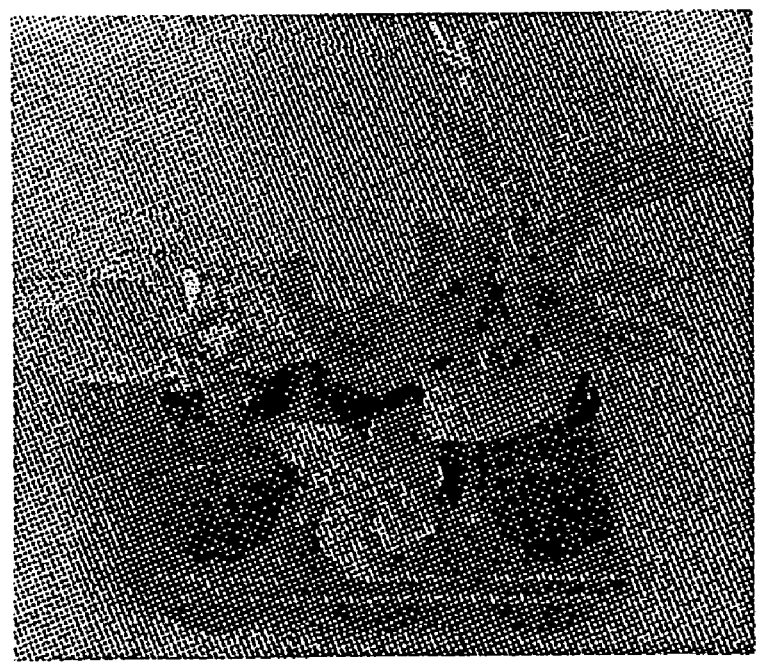

FIG. 8. PURSUIT® imazethapyr Spray Test Results

FIG. 9. Amplification of aadA and snAHAS Fragments

Figure 10A:
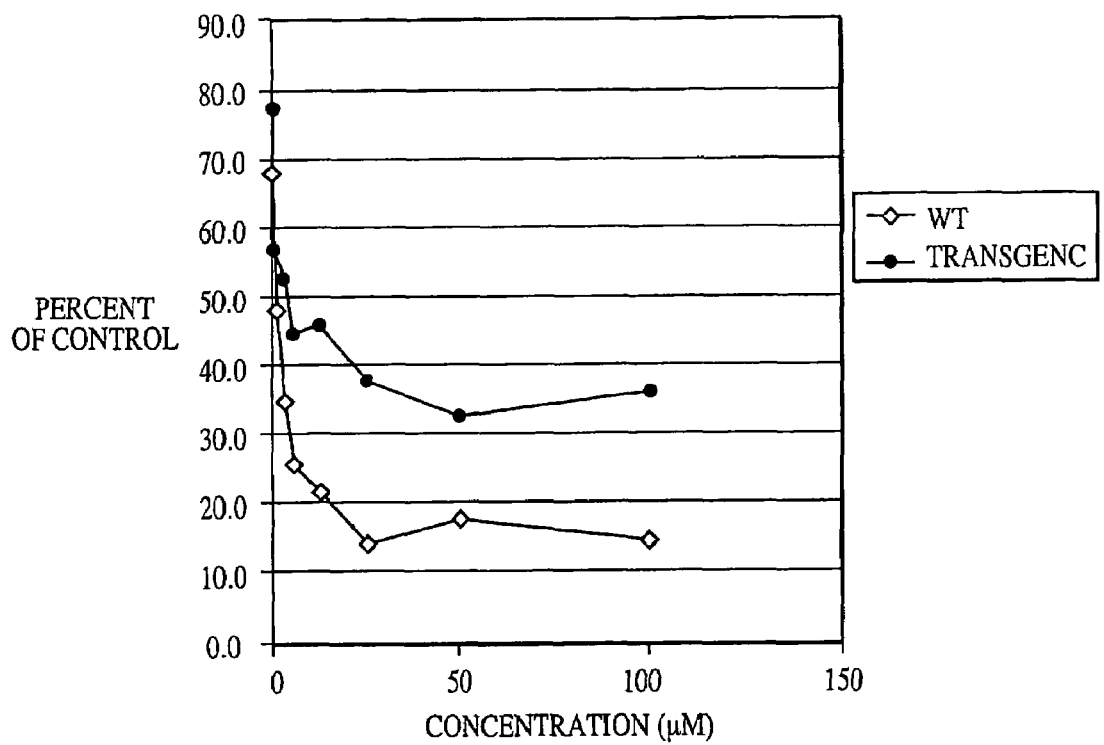
Figure 10B:
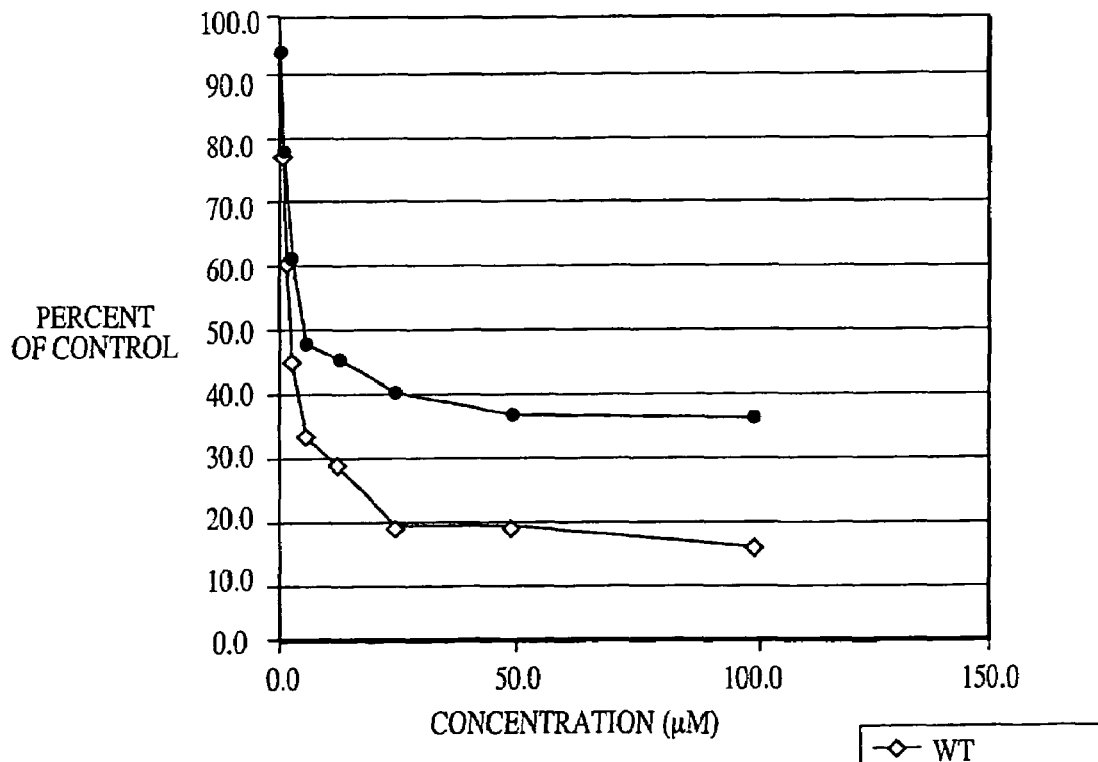

FIG. 10. AHAS Enzyme Assays

Figure 11:
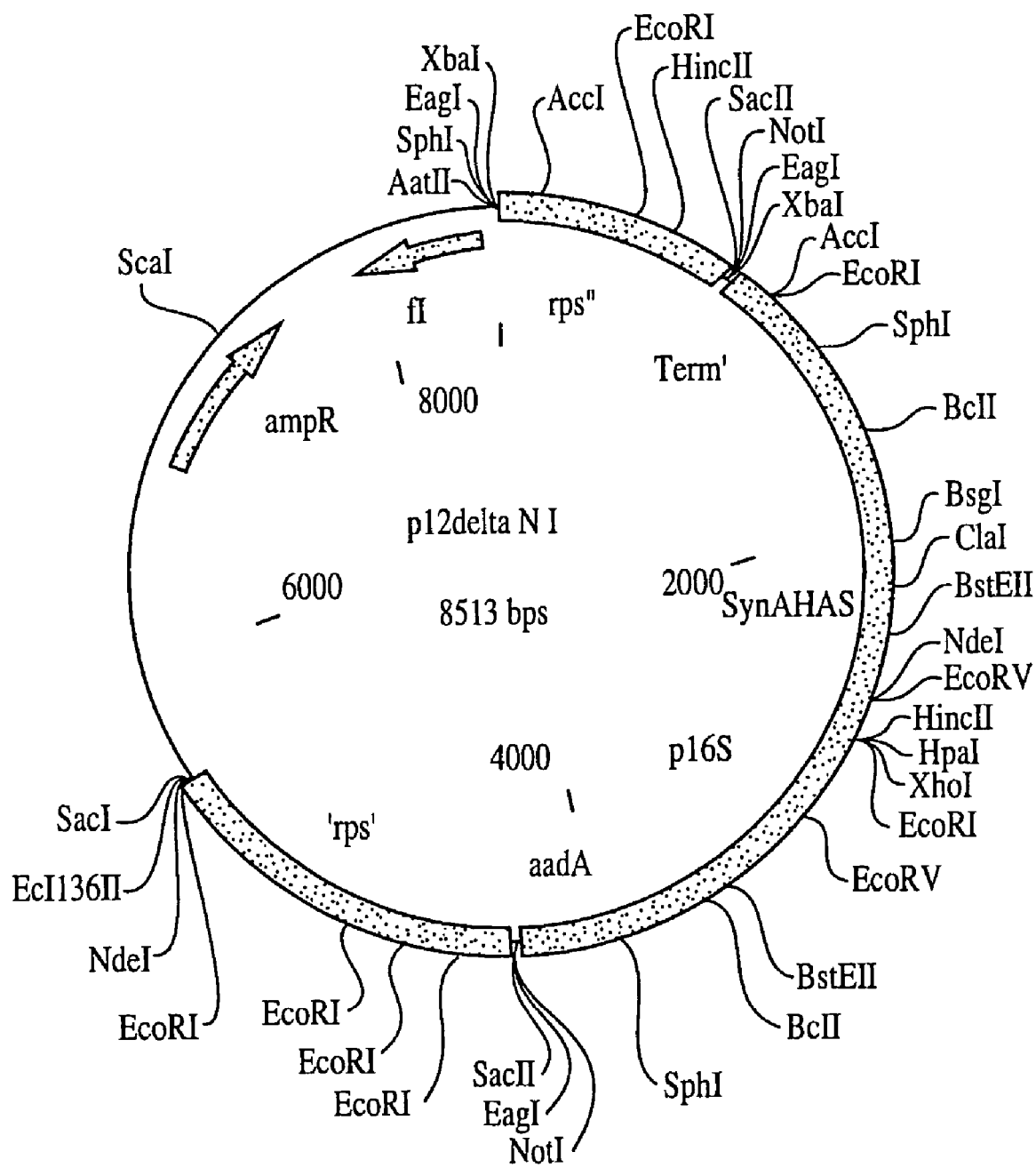

FIG. 11. p1 2deltaNI construct, also known as pACBC111

Figure 12:
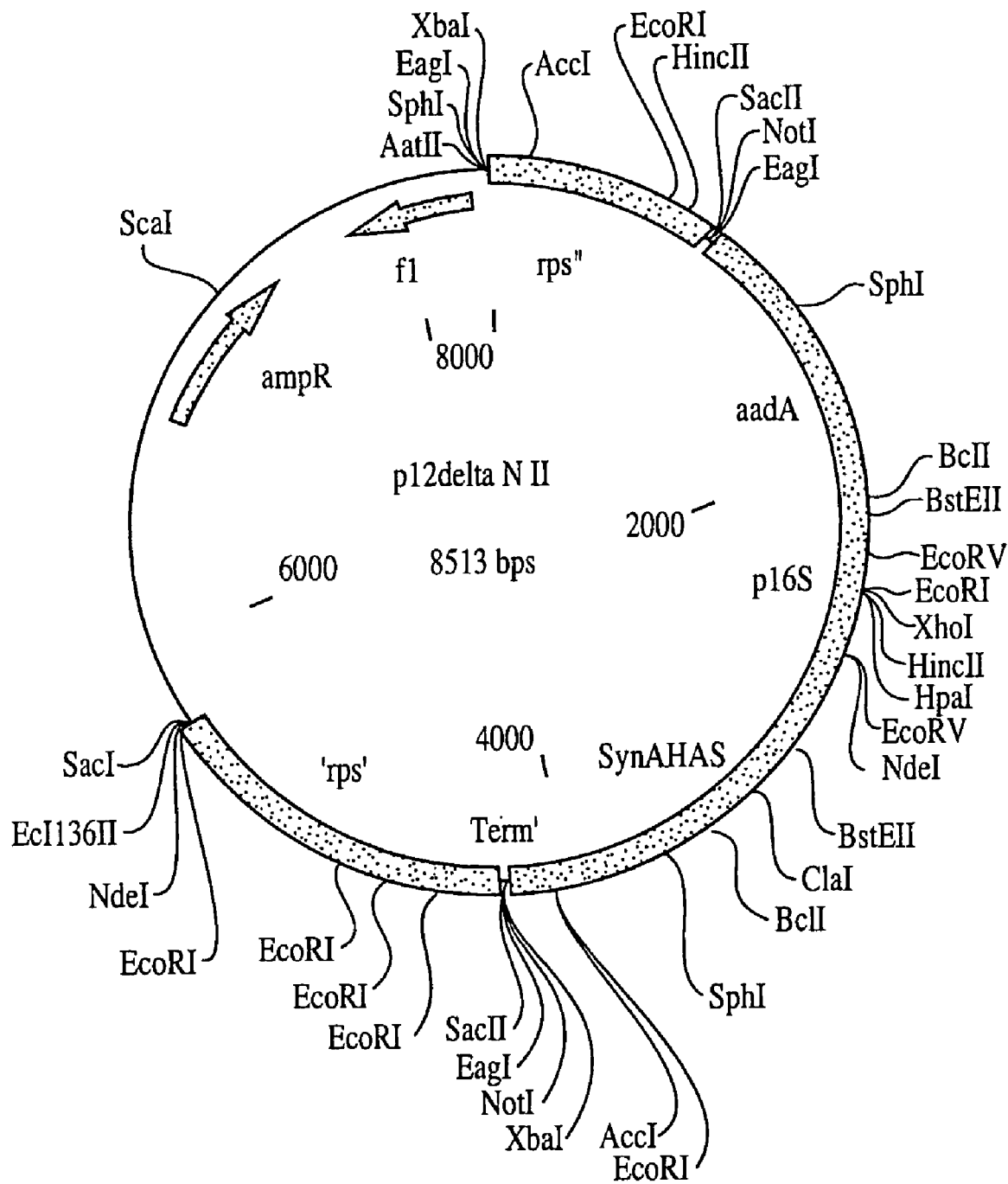

FIG. 12. p1 2deltaNII construct, also known as pACBC112

Figure 13:
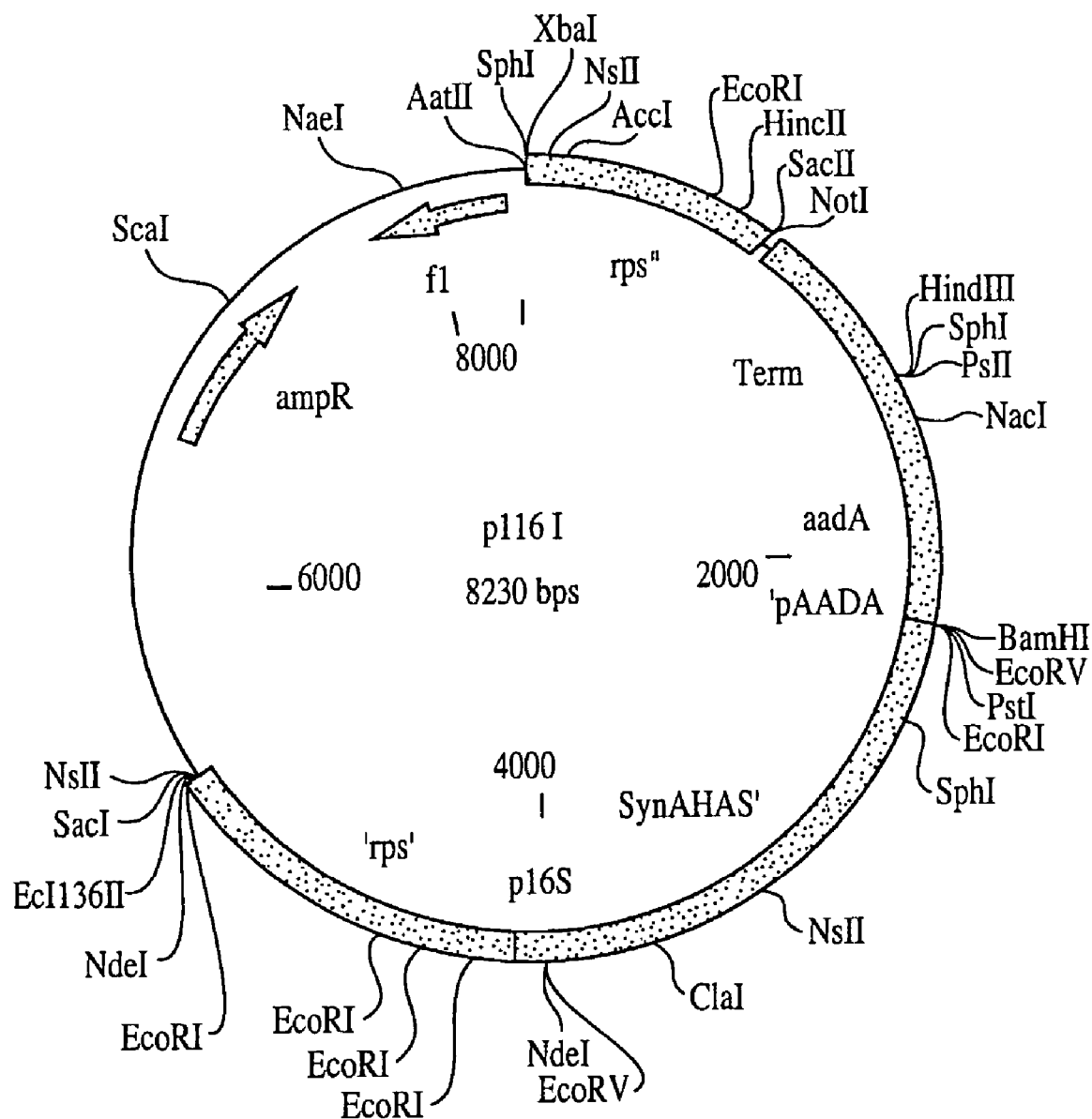

FIG. 13. p1 16I construct

Figure 14:
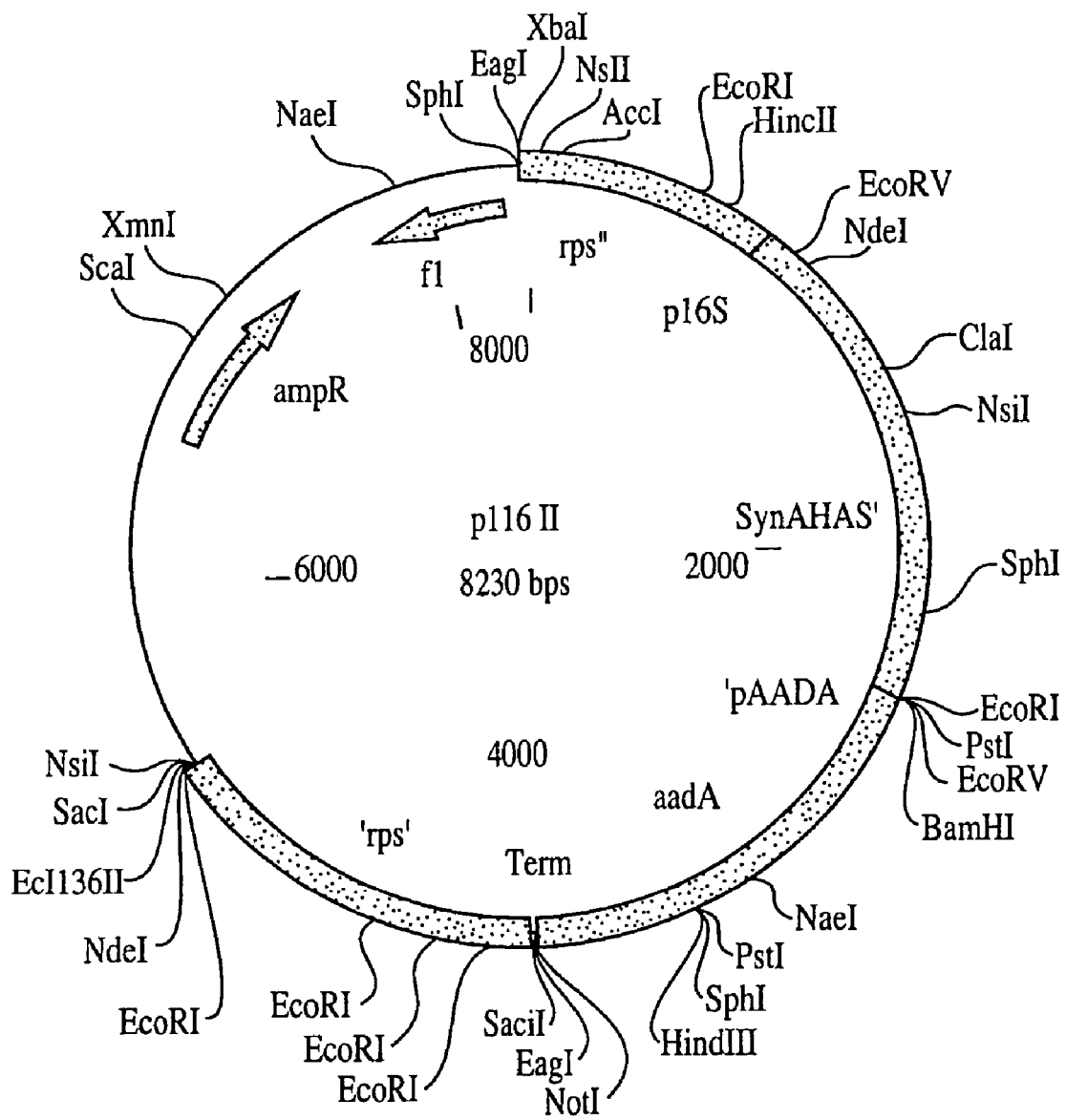

FIG. 14. p1 16II construct

Figure 15:
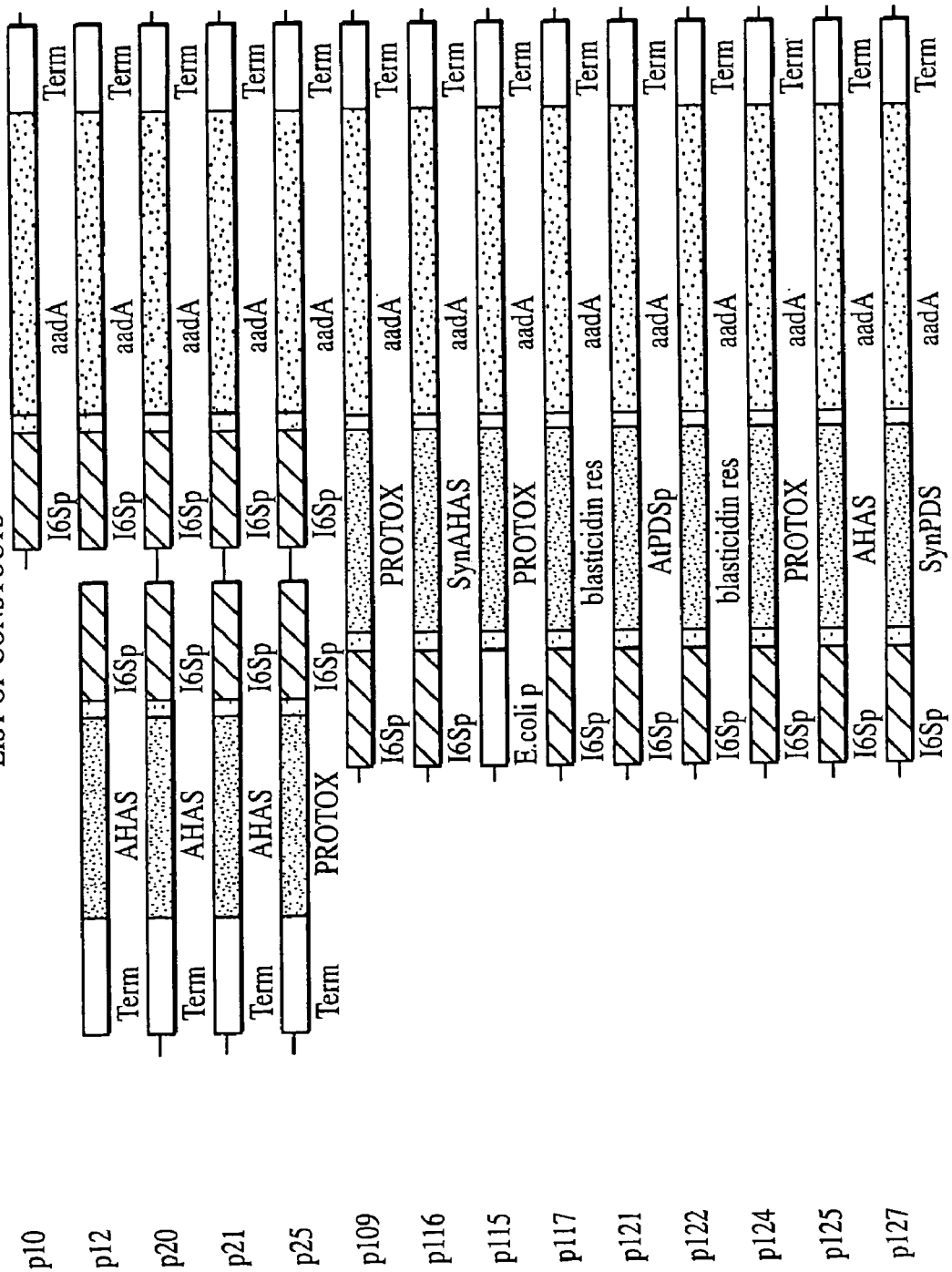

FIG. 15. List of Constructs, including p1 16.

DETAILED DESCRIPTION

A. Rapid Plate Based Assay for Identifying Lead Compounds

A prerequisite to successful utilization of Synechocystis in target site gene discovery is the identification of compounds that affect the metabolism of this organism. To this end, we have developed and established a rapid plate based assay for screening compounds inhibiting phytoene desaturase (pds) activity. In preferred embodiments the present invention provides improvements in the methods utilizing cyanobacteria, a paper disc assay and a microtitre liquid test, for the screening of novel herbicidal modes of action and to identify novel herbicide resistance mutations. Screening can be performed in simple media, preferably BG-11 (sigma, St. Louis Mo.), without the need to maintain axenic conditions. Furthermore, quantitative determinations can be made within one to three days.

Screens can be designed to identity inhibitors of other specific metabolic pathways, which are common only to photoautotrophic cyanobacteria and higher plants and not heterotrophic organisms such as other bacteria.

To identity a target site gene activity, two types of Bluegreen algae, *Synechocystis* PCC 6803 (American Type Culture Collection, Rockville, Md.) and *Anabaena* PCC 7120 (American Type Culture Collection, Rockville, Md.) can be used for the screen. One is grown in microtiter plates in BG-11 medium supplemented with various concentrations of the test compounds. Inhibition of growth can be monitored by visual inspection after two to three days of culture. Quantitative growth measurements can be taken photometrically starting one day after inoculation.

Alternatively screens can be performed on agar plates with "lawns" of cyanobacteria and paper discs impregnated with test compounds. In this case, zones of inhibited growth around paper discs can be detected after two or three days.

To set up the assay, wild type cells of *Synechocystis* were mixed with equal volumes of 2× top agar and 2× BG-11 and overlaid on top of BG-11 agar plate. Cells normally appear in 3-5 days after plating. This method will yield an even and uniform lawn of cells. Upon solidifying, test compounds are then spotted on Whatman filter paper disc before being placed on agar plates. Four compounds can be tested on a single plate. Using this screening, in an example employing 160 different compounds, predominantly compounds of novel mode of action, have been tested on this microbe, and on average, 25% of the compounds show at least some activity.

EXAMPLE 1

Cyanobacterial Screening Process

A rapid plate based assay for screening lead compounds was developed as follows. First, either one of two types of bluegreen algae, *Synechocystis* PCC6803 and *Anabaen* PC 7120 were grown in microtitre dishes containing BG-11 supplemented with various concentrations of 160 different test compounds. Alternatively, screens can be performed on agar plates with lawns of cyanobacteria and paper discs impregnated with test compounds.

Susceptibility of *Synechocystis* to 4'-fluoro-6-[(alpha,alpha,alpha,-trifluoro-m-toly)oxy]-picolinamide was tested using a paper disc assay in which 4'-fluoro-6-[(alpha,alpha,alpha,-trifluoro-m-toly)oxy]-picolinamide was spotted in a paper disc before being placed on a lawn of cells. In determining susceptibility, the size of the zone of inhibition is indicative of the potency of the compound.

These experiments also established a dose-response curve. A lethal concentration for resistant mutant selection was 1-2 μM of 4'-fluoro-6-[(alpha,alpha,alpha,-trifluoro-m-toly)oxy]-picolinamide. Dose-response studies were also performed in 96-sell microtiter plates on wild type and putative 4'-fluoro-6-[(alpha,alpha,alpha,-trifluoro-m-toly)oxy]-picolinamide resistant mutants of *Synechocystis*. The growth of the culture was measured daily at an optical density of 690 nm.

A rapid plate based assay for screening and identifying active compounds is then performed. Wild type cells of *Synechocystis* are mixed with equal volumes of 2× top agar and 2× BG-11. The mixture is then overlaid on top of a BG-11 agar plate. Cells normally appear 3-5 days after plating. This method will yield an even and uniform lawn of cells.

After solidification of the agar, test compounds were spotted on Whatman filter paper disc, and then were placed on agar plates. Four different compounds were tested on a single plate. Using this screening method, 160 different compounds were tested, predominantly compounds of novel mode of action. On average, 25% of the compounds show at least some activity.

B. *Synechocystise* Mutant pds Gene

The protein phytoene desaturase (PDS, encoded by the gene pds) is the target of a number of commercially available bleaching herbicides. The simple Cyanobacterial genetic system, *Synechocystis*, was used to generate and select mutant forms of pds resistant to 4'-fluoro-6-[(alpha,alpha,alpha,-trifluoro-m-toly)oxy]-picolinamide. (BASF (Previously American Cyanamid Company, Princeton, N.J.))

4'-fluoro-6-[(alpha,alpha,alpha,-trifluoro-m-toly)oxy]-picolinamide is a herbicide for the post-emergence control of broad leaf weeds in winter and spring wheat. Its site of action has been determined to be PDS. On BG-11 (Sigma, St. Louis Mo.) solid medium in a paper disc assay, 4'-fluoro-6-[(alpha,alpha,alpha,-trifluoro-m-toly)oxy]-picolinamide was found to be active against *Synechocystis* PCC6803 (Referred to as *Synechocystis*) at concentrations in the 1-2 μM range. Furthermore, *Synechocystis* growth was inhibited with an $I_{50}$ in the lower sub-micromolar range when it was tested in liquid cultures.

Thus, the present invention provides novel *Synechocystis* mutant phytoene desaturase (pds) gene(s) conferring resistance to 4'-fluoro-6-[(alpha,alpha,alpha,-trifluoro-m-toly)oxy]-picolinamide.

The present invention provides a method to isolate and select mutants resistant to 4'-fluoro-6-[(alpha,alpha,alpha,-trifluoro-m-toly)oxy]-picolinamide. Two types of mutants may be isolated, spontaneously produced mutants or chemically induced mutants.

Spontaneous mutants were obtained by growing wild-type *Synechocystis* in liquid culture, or directly plated on plates containing lethal concentrations of 4'-fluoro-6-[(alpha,alpha,alpha,-trifluoro-m-toly)oxy]-picolinamide or through stepwise exposure to increasing levels of 4'-fluoro-6-[(alpha,alpha,alpha,-trifluoro-m-toly)oxy]-picolinamide in liquid culture. Putative resistant colonies were then plated on selection plates to obtain single resistant cell lines.

For isolating chemically induced mutants, ethyl methanesulfone (EMS) may be used. *Synechocystis* cell cultures were treated with EMS at a concentration which gives a 99% killing rate, followed by growth on selection plates. 100-200 ml samples of logarithmic liquid culture were harvested and treated with EMS. The reaction was stopped by addition of sodium thiosulfate, to a final concentration of 5%, to quench excessive EMS. Cells were then collected and washed twice with BG-11. After an overnight recovery in fresh BG-11 medium, cells were plated on solid BG-11 medium containing 1 uM 4'-fluoro-6-[(alpha,alpha,alpha,-trifluoro-m-toly)oxy]-picolinamide.

To select the 4'-fluoro-6-[(alpha,alpha,alpha,-trifluoro-m-toly)oxy]-picolinamide resistant mutants, surviving colonies of the EMS treatment were picked and cultures in BG-11 in 96-well microtiter plates. After 2-4 days growth, cells were replica plated on BG-11 plates containing 0, 2, or 5 µM 4'-fluoro-6-[(alpha,alpha,alpha,-trifluoro-m-toly)oxy]-picolinamide to identify true resistant mutants. FIGS. 1A, 1B and 1C show the results from one set of selection plates. As the concentration of 4'-fluoro-6-[(alpha,alpha,alpha,-trifluoro-m-toly)oxy]-picolinamide was increased from 2 to 5 µM (from FIG. 1B to 1C), the majority of the cells failed to grow. Out of 576 (96×6) putative resistant colonies plated on 5 uM of 4'-fluoro-6-[(alpha,alpha,alpha,-trifluoro-m-toly)oxy]-picolinamide plates, 7 resistant colonies were identified, as shown in FIGS. 2A, 2B, 2C and 2D.

The resistant phenotype of selected mutant cell lines was further tested in solid medium as well as in suspension cultures. Selected resistant colonies were given in-house names to differentiate themselves from one another: 5-1/12E, 5-1/12F, 7-2/1E, 7-3/11F, 7-3/12F, 7-4/12F. FIGS. 3a, 3b, 3c, 3d, 3e, 3f and 3g shows the growth of wild type synechocystis was significantly inhibited at a rate of 4'-fluoro-6-[(alpha,alpha,alpha,-trifluoro-m-toly)oxy]-picolinamide as low as 0.5 nmol whereas the growth of mutant lines was inhibited at a substantially lesser rate. The difference between the wild type and mutant lines becomes even more apparent at the highest rate (5 nmol) tested.

In this particular experiment zones of inhibition for the wild type synechocystis cells were observed at the two higher 4'-fluoro-6-[(alpha,alpha,alpha,-trifluoro-m-toly)oxy]-picolinamide application rates ($5 \times 10^{-10}$ mol and $5 \times 10^{9}$ mol) with a diameter of 20 and 38 nm, respectively. However, zones of inhibition were only observed with 4 of the 6 mutants at the highest rate of 4'-fluoro-6-[(alpha,alpha,alpha,-trifluoro-m-toly)oxy]-picolinamide, results with degree of resistance in the following order: 7-3/11F(0)=7-4/12F(0)>5-1/12E(8)>7-3/12F(12)>5-1/12F(18)>WT(38) (size of zone in nm in parentheses).

In suspension cultures, all mutants exhibit increased resistance against 4'-fluoro-6-[(alpha,alpha,alpha,-trifluoro-m-toly)oxy]-picolinamide. FIG. 4 shows the result from one such dose-response experiment after seven days of culture. For wild type cells (WT), the growth was inhibited at concentrations of 4'-fluoro-6-[(alpha,alpha,alpha,-trifluoro-m-toly)oxy]-picolinamide of <0.25 µM, with an $I_{50}$ in the sub µM range. By contrast, the $I_{50}$ values are between 1-2 µM for 5-1/12E, and in the range of 5-10 µM for 7-3/12F and 7-4/12F, respectively.

Thus, there is substantial evidence that the isolated cell lines confer increased levels of 4'-fluoro-6-[(alpha,alpha,alpha,-trifluoro-m-toly)oxy]-picolinamide resistance.

EXAMPLE 2

Isolation and Selection of Mutant PDS Genes 100-200 ml of logarithmic liquid culture was harvested and treated with mutagen ethyl methanesulfonate (EMS) in a phosphate buffer. To quench excessive EMS, the reaction was stopped with the addition of sodium thiosulfate to a final concentration of 5%. Cells were collected and washed twice with BG-11, then placed in a fresh BG-11 medium for overnight recovery.

The cells were then plated on a solid BG-11 medium containing 1 uM 4'-fluoro-6-[(alpha,alpha,alpha,-trifluoro-m-toly)oxy]-picolinamide. Surviving colonies were cultured in BG-11 within 96-well microtiter plates.

To identify true mutants, cells were replica plated on BG-11 plates containing 0, 2 or 5 µM 4'-fluoro-6-[(alpha,alpha,alpha,-trifluoro-m-toly)oxy]-picolinamide, after 2-4 days growth.

A result from one set of figure plates is shown in FIGS. 1A, 1B and 1C. As the concentration of 4'-fluoro-6-[(alpha,alpha,alpha,-trifluoro-m-toly)oxy]-picolinamide was increased from 2 to 5 µM, the majority of the cells failed to grow. Only 7 resistant colonies were identified out of the 576 (96×6) putative resistance colonies plated on 4'-fluoro-6-[(alpha,alpha,alpha,-trifluoro-m-toly)oxy]-picolinamide. FIGS. 2A, 2B, 2C and 2D.

The resistant phenotype of selected mutant cell lines was further tested in solid medium as well as in suspension cultures. For the solid medium tests, a paper disc assay was done. As shown in FIG. 3, the growth of wild type Synechocystis was significantly inhibited with 0.5 nmol of 4'-fluoro-6-[(alpha,alpha,alpha,-trifluoro-m-toly)oxy]-picolinamide. In contrast, the growth of the mutant lines was inhibited at a lesser rate. The difference between the wild type cells and the mutant cell lines became more apparent with a higher concentration of 4'-fluoro-6-[(alpha,alpha,alpha,-trifluoro-m-toly)oxy]-picolinamide.

In a suspension culture test, all mutants exhibited increased resistance against 4'-fluoro-6-[(alpha,alpha,alpha,-trifluoro-m-toly)oxy]-picolinamide. FIG. 4 shows the result from one such dose response experiment after seven days. Wild type cells were inhibited at concentrations of <0.25 uM 4'-fluoro-6-[(alpha,alpha,alpha,-trifluoro-m-toly)oxy]-picolinamide, with an $I_{50}$ in the sub µM range. In contrast $I_{50}$ values are between 1-2 µM for 5-1/12E and 5-1/12F, and between 5-10 µM for 7-3/12F and 5-4/12F. Thus, because the cell lines with the mutant pds genes are far more resistant than wild type cell lines, there is evidence that the selected cultures contain 4'-fluoro-6-[(alpha,alpha,alpha,-trifluoro-m-toly)oxy]-picolinamide resistance.

A method for the preparation of pds resistant nucleic acid fragments from the cyanobacteria Synechocystis EMS resistant cell lines is provided in additional preferred embodiments.

Genomic DNA was prepared from six Synechocystis EMS resistant cell lines obtained from the isolation and selection process above. A 1.7 Kb Genomic DNA fragment encompassing the pds was amplified using Genomic DNA as a template. PCR amplified pds gene fragments were subsequently subcloned into the Invitrogen TOPO TA Cloning vector pCR2.1-TOPO (Invitrogen Corp, Carlsbad, Calif.) to obtain plasmid pCR2.1-TOPO-PDS.

Cloning of the resistant pds gene into a vector was done as follows. A pair of primers were designed based on sequence information available in a database (the NCBI databases hosted on the government funded NIH server, and search the "Nucleotide" database for the term "X62574" to retrieve the PDS genomic sequence information). The primers had the sequence (from 5' to 3'): X62574-5' cgaattccct ggtagcattt aatacaaatt ggc, identified as Sequence ID NO:1 and X62574-3' cgcataagct ttgcagatgg agacggtttg ggc, identified as SEQ ID NO:2. The primers were used to amplify the pds gene encoding phytoene desaturase, using Synechocystis Genomic DNA (prepared from six Synechocystis EMS resistant cell lines obtained from the isolation and selection process above) as a template. A 1.7 Kb PCR fragment was obtained and subsequently subcloned into Invitrogen TOPO TA vector to generate plasmids TOPO TA-PDS (PDSr).

EXAMPLE 3

Cloning and Subcloning of Mutant PDS Gene

Cloning of the mutant pds genes went as follows. A pair of primers were designed to amplify the pds gene using *Synechocystis* DNA prepared from wild type and 4'-fluoro-6-[(alpha,alpha,alpha,-trifluoro-m-toly)oxy]-picolinamide resistant mutant cells as templates.

PDS genes were cloned from wild type *Synechocystis* and 4'-fluoro-6-[(alpha,alpha,alpha,-trifluoro-m-toly)oxy]-picolinamide resistant cell lines. *Synechocystis* genes were cloned from cell lines by a PCR based strategy. Genomic DNA was used as a template. Based on sequence information available in a database, the following primers were used (from 5' to 3'): X62574-5' cgaattccct ggtagcattt aatacaaatt ggc, SEQ ID NO:1 and X62574-3' cgcataagct ttgcagatgg agacggtttg ggc, SEQ ID NO:2.

A 1.7 Kb PCR fragment was obtained and subsequently subcloned into Invitrogen TOPO TA vector, resulting in plasmids TOPO TA-PDS (PDSr). PCR products were subcloned into an Invitrogen TOPO TA cloning vector, generating TOPO TA-PDS (PDSr). Plasmids carrying pds insertion were prepared using Qiaprep Spin Miniprep Kit. (Qiagen Inc., Valencia, Calif.).

PDS gene PCR products as well as plasmids carrying pds gene derived from all six mutant cell lines were used in a functional complementation assay.

Testing was done to eliminate the possibility that 4'-fluoro-6-[(alpha,alpha,alpha,-trifluoro-m-toly)oxy]-picolinamide resistance was linked to a mutation other than, or in addition to, the phytoene desaturase in *Synechocystis*. Digested *Synechocystis* genome DNA, PCR fragments of PDS gene and TOPO TA-PDSr plasmids were all used in a genetic complementation study. All DNA species tested transformed *Synechocystis* to 4'-fluoro-6-[(alpha,alpha,alpha,-trifluoro-m-toly)oxy]-picolinamide resistance. This suggests that resistance to 4'-fluoro-6-[(alpha,alpha,alpha,-trifluoro-m-toly)oxy]-picolinamide is associated with the mutation in the pds gene in these mutant cell lines.

Three independent clones were picked and sequenced for each mutant cell line. Sequencing of PCR amplified pds gene product from resistant cell line 7-4/12F revealed a single base pair change of G⇒A at position 642 (position 523 within ORF) (Table 1), resulting in an amino acid change of Ala⇒Thr at position 175. The sequence is identified as Sequence ID NO:3. This mutation is unique and different from the only mutation (Arg$^{195}$⇒Cyr, Pro, or Ser) described in the pds gene from *Synechocystis* by Martinez-Ferez et al, 1994, and four other point mutations (Arg$^{195}$⇒Pro, Leu$^{320}$⇒Pro, Val$^{403}$⇒Gly, Leu$^{436}$⇒Arg) previously reported for the pds gene from *Synechococcus* sp. PCC7942. All of the previously described mutations were identified based on their ability to confer resistance to the commercial herbicide norflurazon to wild type cells.

TABLE 1

List of point mutations in herbicide resistance-conferring pds genes from cyanobacteria

| Amino Acid Position | Mutation | A.A. substitution | Source | Target Herbicide | References |
|---|---|---|---|---|---|
| 175 | G ⇒A | Ala ⇒Thr | *Synechocystis* | 4'-fluoro-6-[(alpha,alpha,alpha,-trifluoro-m-toly)oxy]-picolinamide | This work |
| 195 | C ⇒T | Arg⇒ Cys | *Synechocystis* | norflurazon | Martinez-Ferez & Vioque 1992 |
| 195 | C ⇒A C ⇒T G ⇒C | Arg ⇒Ser Arg⇒ Cys Arg ⇒Pro | *Synechocystis* | norflurazon | Martinez-Ferez et al 1994 |
| 403 | T ⇒G | Val ⇒Gl | *Synechococcus* | norflurazon | Chamovitz et al 1991 |
| 195 320 436 | G ⇒C T ⇒C T ⇒C | Arg ⇒Pro Leu ⇒Pro Leu ⇒Arg | *Synechococcus* | norflurazon | Chamovitz et al 1993 |

EXAMPLE 4

Sequencing of Mutant PDS Gene

Three independent clones were picked and sequenced using the dRhodamine Terminator cycle Sequencing Kit. (PE Biosystems, Norwalk, Conn.). The reactions were analyzed in an ABI A310 Genetic Analyzer (ABI, Foster City, Calif.). Sequencing the PCR amplified pds gene product from resistance cell line 7-4/12F revealed a single base pair change of G⇒A at position 642 (position 523 within ORF). See Table 1. This results in an amino acid change of Ala⇒Thr at position 175. The mutation is unique. It is different from the only mutation described in the pds gene from *Synechocystis* (ARG195⇒Cys, Pro or Ser), and four other point mutations previously reported for the pds gene from *Synechococcus* sp. PCC7942 (Arg195⇒Pro, Leu320⇒Pro, Val403⇒Gly, Leu436⇒Arg). All of those mutations were identified based on their ability to confer resistance to commercial herbicide norflurazon to wild type cells.

The complete sequence of the novel mutant form pds gene, identified as SEQ ID NO:3, reads as follows:

```
   1 ccctggtagc atttaataca aattggctat cttggcaaag tcccccgaaa tattacgaaa
  61 cgtaaagtat aataacaatc aacctgtaaa ccccaaatgc cttagcgaga cagtaaccca
 121 tgcgcgttgt gatcgccgga gccggattag ccggcctagc ctgtgccaaa tacttagccg
 181 atgcgggctt taccccgtc gtcttggaac gtagggatgt attaggcggg aagatcgccg
 241 cgtggaaaga tgaggacgga gattggtacg aaaccggcct acacattttt tttggggcct
 301 atcccaacat gttgcagtta tttaaggaat tggatatcga agatcgtctg caatggaaag
 361 agcacagcat gatcttcaac caaccagaga aaccaggtac ctactctcgg ttcgattttc
 421 cggatattcc ggcccccatc aatggtttgg tagccattct tcgcaacaac gatatgctta
 481 cctggccgga gaaaattcgc tttggcttgg gactcttgcc ggccattgtc cagggccaga
 541 gctatgtgga agaaatggat aaatacactt ggtcagagtg gatggccaaa caaaatattc
 601 cccccgcat cgaaaagaa gttttcattg ccatgagtaa gacgttgaac tttattgatc
 661 ccgatgaaat ttccgccacc attttactta ctgccctcaa tcgcttttta caggaaaaaa
 721 atggctctaa gatggcattc ctggatgggg caccaccgga gcgtctttgc caacctttgg
 781 tcgactatat tacggaacgg ggaggggaag tacacattaa taaacctctc aaagaaattt
 841 tgcttaatga agatggttcc gttaagggtt acttaatccg gggcctagat ggagcccccg
 901 acgaagtgat cacagcggat ttatatgtgt ctgccatgcc ggtggatccc ctgaaaacca
 961 tggtgccagc gccctggaga gaatatcctg agtttaagca aatccaaggt ttggaaggag
1021 tcccggtcat taacctccac ctgtggtttg accgtaagtt aaccgacatt gatcatttgt
1081 tattctcccg atcgccgttg ttgagtgttt acgccgacat gagcaacacc tgccgagaat
1141 acagtgatcc agacaaatcc atgttggaat tggtgctggc tccggcccag gattggatcg
1201 gcaaatccga cgaagagatt gtggcggcca ccatggcgga gatcaagcaa ctctttcccc
1261 aacacttcaa cggggataat ccagcccgac tgcttaaatc ccacgtggtc aaaaccccc
1321 gctcagtcta caaagctacc cccggaaggc aggcttgtcg ccccgatcaa cggacatcgg
1381 tgcccaactt ttacctagca ggggacttca ccatgcaaaa atacttgggc agtatggaag
1441 gggcggtgct ttccggcaaa caatgcgccc aggcgatcgc cgccgatttc aaccccaaa
1501 ccgttccccc caccagggaa atagtcaccg tgggttaagc cgcctggact ccctggtaat
1561 cttcctgaca aatggcaacc ctaatgcgac aatgctaaat ggctaacggt caaatttctc
1621 cccagcgtgc agttaccaaa ccccaatcct ggtggctgac ttccgaaccc cgtccgtcct
1681 taatgttaca actgcccaaa ccgtctccat ctgcaaagcc ctgtgcttct gttga
```

The 5' PCR primer with an engineered EcoR I (Promega) site was highlighted in bold, and that of the 3' PCR primer with an engineered Hind III (Promega) site was also bold typed.

In further embodiments we provide a method for the improved genetic transformation of *Synechocystis*. In the literature, transformation of *Synechocystis* has been performed using either one of the two approaches, "in situ" dot transformation first reported by Dzelzkalns & Bogorad (The *EMBO J.*, 1998, 7: 333-338), and liquid culture based transformation (ref. Williams, *Methods in Enzymology* 1988, 167: 766-778). For the liquid culture based procedure, DNA samples were mixed with fresh cells of *Synechocystis* and incubated for certain period of time before being spread onto membrane filters resting on BG-11 agar plates. After an extended incubation of the plates under standard conditions for the expression of inserted gene(s), the filters were transferred to plates containing selection agents. This is a lengthy procedure and may not be suitable for High-Through-put transformation.

The "in situ" dot transformation procedure entails direct application of DNA sample (restriction fragments, cloned plasmids) in liquid or melted agarose onto a lawn of *Synechocystis* 6803 cells containing selection agents. It is quick and convenient, but cells were not given the time to express the inserted gene before being exposed to selection agents, this procedure is also "destructive" in that DNA samples will be lost regardless of transformation results.

*Synechocystis* DNA was prepared using the Qiagen Dneasy Plant Mini Kit (Qiagen, Valencia, Calif.) following NaI pretreatment and digestion with lysozyme as describes in Williams (1988). For manipulation of DNA in *E. coli*, standard recombination procedures were followed.

A much-improved method was developed in our laboratory to overcome the limitations of the 'in situ' dot transformation and the liquid culture based transformation methods. To transform *Synechocystis*, competent cells were arrayed in 96-well plates. The DNA species to be transformed were then added and mixed with the cells. The 96-well plates containing mixtures of DNA and cells were then placed in Sumilon plate (Vangard International Inc., Taipei, Taiwan) moistened with wet sterile paper towels. Cells were replica-plated at various times onto selection plates containing various concentration of the same or different selection agents. This method is extremely suitable for performing transformations and screening of a large number of samples, such as with the High-Through-Put protocol in Section C.

Transformation of wild-type *Synechocystis* with either DNA species results in enhanced 4'-fluoro-6-[(alpha,alpha,alpha,-trifluoro-m-toly)oxy]-picolinamide resistance. This reinforces the notion that resistance in the original cell lines is the result of mutation within the pds gene.

Also provided for in preferred embodiments is 4'-fluoro-6-[(alpha,alpha,alpha,-trifluoro-m-toly)oxy]-picolinamide resistant mutants which show cross-resistance against other PDS inhibitors. These mutants, when tested against another herbicides which are PDS inhibitors, compound (2E)-2-[amino(benzylsulfanyl)methylene]-1-(2,4-dichlorophenyl)-1,3-butanedione and two of its analogs, pyridine, 2-[(3,3-dichloro-2-propenyl)oxy]-4-methyl-6-[(2-(trifluoromethyl)-4-pyrodinyl]oxy] and 1,2,4,5-benzenetetracarboxamide,N,N',N'',N'''-tetrakis[5-(benzoylamino)-9,10-dihydro-9,10-dioxo-1-anthracenyl], exhibited cross-resistance.

C. High-Through-Put Target Site Gene Identification using *Synechocystis*

In this invention, we further describe the successful development of various protocols for High-Through-Put (HTP) molecular manipulation of *Synechocystis*. These include but not limited to procedures such as lead compound identification, generation and selection of resistant mutant, HTP genetic transformation and functional complementation. As a result, it is now possible to design a program for rapid and cost effective identification of target site genes using this microbe.

As illustrated in FIG. 5, a prerequisite to the successful implementation of this program is the identification and availability of lead chemicals active on this microbe. Resistant mutants can be generated and selected against the compounds of interest using a chemical based approach. To isolate the resistance-conferring gene, one of the most commonly adopted practices has been the gel fractionation method. This method entails the following steps: (1) digestion of genomic DNA prepared from mutant cell cultures of *Synechocystis*, (2) fractionation of digested DNA on agarose gel and purification of DNA from gel slices, (3) identification of positive fraction through $1^{st}$ round of functional complementation, (4) construction of a gene library, (5) preparation of plasmid DNA from single colonies, and (6) identification of target gene in $2^{nd}$ round of functional complementation. This is a very time-consuming process. There is a possibility that the resistance-conferring fragment may not be the right size for complementation assay and/or for subsequent subcloning into library vector. Consequently, the gene fragment of interest may never be found in the gene library. By contrast, a preferred embodiment of the High-Through-Put program requires the preparation of ~1800 primer pairs for amplification of 1800 overlapping 2-kb fragments (the size of the fragment, thus the total number of primers, may be altered for easy PCR amplification and HTP manipulation) to cover the complete genome of *Synechocystis* (~3.6 Mb). It entails rapid amplification of 1800 fragments using genomic DNA from *Synechocystis* mutant cell lines.

A size range of 1.5-3 kb would be ideal, both for PCR amplification and homologous recombination in *Synechocystis*. PCR products that are too small would compromise the efficiency of transformation in this microbe. On the other hand, it is more difficult to amplify bigger gene fragment using PCR. Some trial and error adjustment can be made as needed in a particular PCR system according to methods well known to those skilled in the art. This process can be adapted to any organisms (e.g. Yeast *S. cerevisiae* or other cyanobacteria) for which the whole genome sequence information is known and transformation through homologous recombination is feasible.

PCR products can then be used for HTP transformation of *Synechocystis* and functional complementation assay on various selection plates, using methods well-known to those skilled in the art. Gene(s) conferring herbicide resistance can then be identified based on the ability of its PCR products to confer herbicide resistance to wild type cells upon transformation. All of which can be performed using 96-well microtitre plates, in addition, only one round of transformation is needed to identify the resistance-conferring gene. Some major steps in this process are detailed below:

(1) Lead compounds identification: This can be done in a reasonably high through put manner using either the paper disc assay on solid BG-11 agar plate or 96-well microtiter plate as described in Section A and Example 1.

(2) Generation and isolation of resistant mutant(s): *Synechocystis* mutant(s) resistant to compound of interest can be generated chemically by treating cultures of *Synechocystis* with chemical mutagens (e.g. EMS). Procedures for performing such experiment are provided in Section B and Examples 2 & 3.

(3) Isolation of genomic DNA from resistant cell lines: Genomic DNA can be prepared from cultures of *Synechocystis* resistance cell lines using commercial kits (e.g. Qiagen DNAeasy Plant Kit) as described in Section B.

(4) Primer design and PCR amplification of gene fragments from *Synechocystis*: Primer pairs for amplification of overlapping DNA fragments from *Synechocystis* can be designed with the assistance of a commercial software package (e.g. Vector NTI from InforMax, North Bethesda, Md.). Large-scale synthesis of primers can be done by a commercial vendor (e.g. Sigma-Genosys, The Woodlands, Tex.) in 96-well format. PCR amplification of ~1800 2-kb fragments (again, the size of the fragment, thus the total number of primers may be altered for easy PCR amplification and HTP manipulation) can be performed using genomic DNA prepared from mutant cell cultures as template following standard laboratory procedures, as explained in Section B and Example 3.

(5) High Through Put genetic transformation and target site gene identification: Procedures for HTP genetic transformation and functional complementation assays have been described in Section B. Gene(s) conferring herbicide resistance can then be identified based on the ability of its PCR products to confer herbicide resistance to wile type cells upon transformation.

This program offers the flexibility of working with more than one active compound at a time. This flexibility occurs because of the ease with which one can replica-plate cells on plates containing different selection compounds, at different time upon transformation with PCR products. Conceivably, this will be a very high through put process for the rapid identification of target site genes once active compounds are identified.

D. *Synechocystis* AHAS Genes

AHAS Physical Properties

Cyanobacteria are a particularly useful source of genes for enhancing crop performance due to their similarity, and ancestral connection, to plant chloroplasts. In particular, cyanobacterial genes may be useful for transformation directly into the chloroplast genome due to similarities in genetic elements. Similarities in cyanobacterial genes and proteins to those from chloroplasts can carry over to a shared susceptibility to herbicides. *Synechocystis* PCC 6803 was demonstrated to be susceptible to several known herbicides as shown in Table 2 as described in detail below.

TABLE 2

| Compound | Activity Rating (++ = highest) | Target Site |
| --- | --- | --- |
| Maleic Hydrazide | ++ | Carotenoid biosynthesis |
| Simazine | ++ | Photosynthesis |
| Fenuron | ++ | ? |
| Monuron | ++ | Phytosynthesis |
| CMU | + | Phytosynthesis |
| Desmedipham | ++ | ? |
| Bromoxynil | + | Photosynthesis/Respiration |
| Phenmedipham | ++ | ? |

In cases where cyanobacteria are susceptible, they are good organism for use in screening for mutations that confer resistance due to the readily available methods for genetic manipulation such as transformation, high throughput screening, liquid or agar based selection, replica plating, shuttle vectors, a small, and in some cases a completely sequenced, genome. The mutated gene sequences that are isolated after selection for resistance can be transformed into the nucleus or plastome of plants, or alternatively, the functional equivalent of identified mutations can be inserted into genes from plants or other organisms for use in transformations.

In some cases cyanobacteria are insensitive to herbicides, potentially due to difference in uptake, metabolism, or differences in the target protein. Consequently, genes from cyanobacteria may be useful in conferring herbicide resistance to plants of interest.

AHAS Biochemistry

The end products of the branched chain amino acid biosynthetic pathway (isoleucine, leucine, and valine) feedback inhibit Acetohydroxyacid synthase (AHAS) activity. Only the large subunit has catalytic activity.

It has been established in the literature for many years that microbial AHAS enzymes, in-vivo, exist as two distinct but physically associated protein subunits. The two polypeptides, a "large subunit" and a "small subunit" are expressed from separate genes. From the study of AHAS enzymes from microbial systems, two roles have been described for the small subunit: 1) the small subunit is involved in the allosteric feedback inhibition of the catalytic large subunit when in the presence of isoleucine, leucine or valine and, 2) the small subunit enhances the activity of the large subunit in the absence of isoleucine, leucine or valine. For example, the large subunit alone has a basal level of activity that cannot be feedback inhibited by amino acids. When the small subunit is added, the level of activity of the large subunit increases. If the small subunit is included with isoleucine, leucine or valine, the activity is below that of the basal level with large subunit alone.

Since activity of prokaryotic AHAS large subunits have been shown to be suboptimal in the absence of small subunits, the level of activity of the *Synechocystis* AHAS large subunit, and its ability to confer herbicide resistance, may be suboptimal without co-expression of a small subunit gene.

The sequence of the entire genome of the cyanobacterium *Synechocystis* PCC6803 has been determined, published, and can be accessed via NCBI databases hosted on the government funded NIH server, and search the "Genome Project" database for the term "*Synechocystis*". When the genome of *Synechocystis* PCC6803 was published, subsequent to cloning of the original AHAS large subunit gene, a search was done on the genome for other AHAS genes. The search found an additional gene with a high degree of homology to AHAS sequences. This gene in *Synechocystis* is designated sll1981 and annotated as ilvB.

However, prior to the publication of ilvB sequence, we cloned a novel *Synechocystis* AHAS Large Subunit Gene nucleic acid fragment cloned from a genomic DNA library of cyanobacterium *Synechocystis* PCC6803. This original gene that was cloned is identified as slr2088 and annotated as ilvG. Susceptibility tests show that AHAS activity is resistant to imidazolinones such as PURSUIT® imazethapyr (BASF, formerly American Cyanamid, Princeton, N.J.) and sulfonylureas such as OUST® sulfometuron methyl (DuPont, Wilmington, Del.).

In vivo resistance of cyanobacteria to PURSUIT® imazethapyr and OUST® sulfometuron methyl. As a preliminary matter, *Synechocystis* PCC6803 and *Anabaenia* PCC7120 were tested for susceptibility to PURSUIT® imazethapyr and OUST® sulfometuron methyl. AHAS genes which are resistant to these herbicides are excellent candidates for transformation in plant plastomes and nuclear genomes. Such transformants can be used in a weed control strategy using a combination of transgenic herbicide resistant crops and herbicides.

In vivo testing of *Synechocystis* PCC6803 and *Anabaena* PCC7120 was done by culturing the organisms in varying concentrations of the commercial herbicides. Both organisms demonstrated a high degree of insensitivity to the compounds (FIG. 6). No inhibition of growth was seen at concentrations of 100 µM PURSUIT® imazethapyr or 100 nM OUST® sulfometuron methyl after one week of culture in BG-11 media. For relative comparison purposes a concentration of 1 µM PURSUIT® imazethapyr in agar media is lethal to *Arabidopsis* plants.

In Vitro Resistance of Cyanobacterial Acetohydroxyacid Synthase to PURSUIT® Imazethapyr and OUST® Sulfometuron Methyl AHAS is the target site of both PURSUIT® imazethapyr and OUST® sulfometuron methyl herbicides. To determine if resistance to the herbicides is due to a natural resistance to inhibition of the acetohydroxyacid synthase enzymes from the cyanobacteria, or if it is due to alternative mechanisms (e.g. lack of entry into the cell), the in vitro activity of the AHAS enzyme in the presence of the herbicides was tested.

AHAS assays were performed with slight modification as described by Singh et. al (Singh B K, Stidham M A, Shaner D L, 1988, Assay for acetohydroxyacid synthase from plants. Anal Biochem 171: 173-179).

Results from the in vitro assays (FIG. 7) demonstrates that both *Synechocystis* and *Anabaena* AHAS enzymes are insensitive to inhibition by the herbicides. The $I_{50}$ of plant AHAS enzymes are normally in the range of 1-2 μM for imidazolinones and 10 nM for sulfonylureas (Singh, B. K., Stidham, M. A., and Shaner, D. L., J. Chromatogr., 444,251, 1988). No significant inhibition of the cyanobacterial AHAS enzymes was observed at concentrations of 100 μM PURSUIT® imazethapyr and 100 nM OUST® sulfometuron methyl.

The data shown in FIG. 7 indicated that resistance to AHAS inhibiting herbicides could be attributed to the natural resistance of the target enzyme. Thus, cyanobacterial AHAS genes would be good candidates for transformation into plants, either by nuclear or plastid transformation, for conferring herbicide resistance.

Also, there is a level of cross-resistance exhibited between PURSUIT® imazethapyr and sulfanylcarboxamides. As discussed below, certain lines transformed with the p116 plasmid constructs (FIG. 9) described in detail below, when sprayed with 18 g/ha PURSUIT® imazethapyr showed about a 20% increase in plant resistance in the presence of PURSUIT® imazethapyr and sulfanylcarboxamides when compared with wild type tobacco. Interestingly, it appears that the *Synechocystis* AHAS enzyme displays a level of cross resistance to both PURSUIT® imazethapyr and sulfanylcarboxamides, although the herbicides are both quite dissimilar structurally.

EXAMPLE 5

In Vitro Resistance of Cyanobacterial Acetohydroxyacid Synthase to PURSUIT® Imazethapyr and OUST® Sulfometuron Methyl Experiments were done to determine in vitro resistance of cyanobacterial acetohydroxyacid synthase to PURSUIT® imazethapyr and OUST® sulfometuron methyl.

*Synechocystis* PCC6803 and *Anabaena* PCC7120 were cultured in 1.5 L of BG-11 media. Cells were collected by centrifuge and stored frozen at −80° C. Frozen cells were thawed and placed in a 30 mL Bead Beater cell disruptor chamber (BioSpec Corp Bartlesville, Okla.). Seven mL of acid washed sand was added. The chamber was filled with 2× ASHA assay buffer, consisting of 100 mM HEPES pH7.0, 200 mM pyruvate, 20 mM $MgCl_2$, 2 mM TPP (Thiamine pyrophosphate) and 100 μM FAD (flavin adenine dinucleotide).

The Bead Beater cell disruptor was packed in ice and turned on for 10 seconds, followed by cooling for 3 minutes. This cycle was repeated five times. The extract was transferred into a centrifuge tube, and spun in a Beckman SA20 (Beckman, Fullerton, Calif.) rotor for 15 minutes at 17,000 rpms.

The supernatant was decanted and used for AHAS assays. The assays were performed with slight modification as described by Singh et. Al (Singh B K, Stidham M A, Shaner D L, 1988, Assay of acetohydroxyacid synthase from plants. Biochem 171: 173:179). AHAS activity was assayed in a final concentration of 1× AHAS buffer, except HEPES was used instead of phosphate buffer that Singh used. All assays containing PURSUIT® imazethapyr, OUST® sulfometuron methyl or associated controls contained a final concentration of 5% DMSO (Dimethyl sulfoxide) due to addition of the herbicides to the assay mixtures as a 50% DMSO stock. Assays were performed in a final volume of 250 μL at 37° C. in microtiter plates for one hour.

Isolation of the *Synechocystis* AHAS Large Subunit Gene

The sequence of the coding and flanking regions of the isolated cyanobacterial AHAS gene of the present invention, which confers resistance to PURSUIT® imazethapyr and OUST® sulfometuron methyl, was determined.

A probe for identifying the *Synechocystis* AHAS gene was generated by PCR with degenerate primers. To develop these degenerate primers, alignments were made of known AHAS sequences from plants, bacteria, and other cyanobacteria, such as *Spirulina platensis* (M75907.Gb_BA and M75906.Gb_BA, GenBank, National Center for Biotechnology Information). It was found that the predicted amino acid sequences of AHAS protein shared many conserved regions. Thus primers were chosen in regions where amino acid sequences were highly conserved. Degenerate primer were used to allow for differences in the cyanobacterial codon usage. One of the primer pairs, identified as SEQ ID NO:4 and SEQ ID NO:5, respectively had a sequence of:

```
#21:
5' GG(AGCT)AC(AGCT)GA(TC)GC(GACT)TT    (SEQ ID NO:4)
(TC)CA(AG)GA 3'

#19:
5' (CT)T(CG)CCA(CT)TG(AGCT)C(TG)       (SEQ ID NO:5)
(AGCT)ACCAT 3'
```

Genomic DNA was isolated from *Synechocystis* PCC6803 (ATTC#27150) according to Methods in Enzymology 167, p 703-712 and was a template for PCR amplification of an AHAS fragment. The 1 kb PCR product corresponded in size to the fragment these primers would produce based on the distance between the two conserved regions from which the primers were designed. The fragment was isolated and cloned into the pCRII vector (Invitrogen). The insert was partially sequenced and the sequence was found to have strong homology to both of the *Spirulina* AHAS sequences (about 80% similarity and about 70% identity at the amino acid level between the *Synechocystis* sequence and the sequence from the M75907.gb_BA and the *Synechocystis* sequence and the sequence from the M75906.Gb_BA *Spirulina*.)

EXAMPLE 6

Isolation of the *Synechocystis* Large AHAS Gene

A probe for identifying the *Synechocystis* AHAS gene was generated by PCR with degenerate primers. Genomic DNA was isolated from *Synechocystis* PCC6803 according to the method outlaid in Methods in Enzymology 167, p/703-712. PCR was performed with DNA polymerase (Perkin Elmer AmpliTaq, Perkin Elmer, Shelton, Conn.) using this genomic DNA as the template and a series of degenerate primers that were designed from the conserved regions observed in the alignment of AHAS gene sequences in Genbank. One of the primer combinations, identified as Sequence ID NO:4 and Sequence ID NO:5, respectively:

```
#21:
5' GG(AGCT)AC(AGCT)GA(TC)GC(GACT)TT(TC)CA(AG)GA 3'

#19:
5' (CT)T(CG)CCA(CT)TG(AGCT)C(TG)(AGCT)ACCAT 3'
``` produced a 1.1 kb PCR product that corresponded in size to the fragment these fragments would produce, based on the sequences of the two AHAS genes from the cyanobacterium Spirulina platensis. The fragment was isolated and cloned in a pCRII vector (Invitrogen). The insert was amplified and partially sequenced, and was found to have strong homology to both of the Spirulina AHAS sequences, about 80% similarity, 70% identity at the amino acid level.

Library Screening

A genomic library from *Synechocystis* PCC6803 in the Lambda ZAP vector (Stratagene, La Jolla, Calif.) was screened for the AHAS gene. To obtain the probe for screening the *Synechocystis* genomic library, the plasmid isolated in the above procedure was digested with EcoRI (Promega) and the resulting 1.1 kb fragment was gel isolated and purified (GeneClean, Bio 101, Qbiogene, Carlsbad, Calif.). This material (25-50 ng) was labeled with $^{32}$P following the Oligolabelling Kit standard Protocol (Pharmacia, Piscataway, N.J.). Thus labeled, the 1.1 kb fragment was used as a probe to screen for the AHAS gene in the Lambda Zap vector genomic library.

The *Synechocystis* PCC6803 Genomic Library was plated on three plates (NZCYM media) (Sambrook, Fritsch, Maniatis "Molecular Cloning—a Laboratory Manual $2^{nd}$ ed" 1989) at a titer of 5×10$^3$ pfu/plate. Duplicate filters (BA-S NC, Schleicher & Schuell) were lifted from each of the plates. The 15 cm nitrocellulose filters were incubated in 0.5 N HaOH/1.5 M NaCl for 90 seconds, 0.5 M tris8/1.5 M NaCl for 5 minutes, and then 2× SCC (Sodium chloride, Sodium citrate, pH 7.0) (Sambrook, Fritsch, Maniatis *Molecular Cloning—A Laboratory Manual* $2^{nd}$ Ed. 1989) for 5 minutes.

The filters were then air dried and baked in a vacuum oven at 80° C. for two hours. Afterwards, the filters were prehybridized in 50 ml of prehyb solution (50% deionized formamide 5× SCC, 2× Denhardt's solution (Sambrook, Fritsch, Maniatis *Molecular Cloning—A Laboratory Manual* $2^{nd}$ Ed. 1989), 0.1% SDS and 100 ug/ml salmon testes DNA) for 2 hours at 32° C. The filters were then hybridized overnight in a shaking water bath at 42° C. with the labeled probe.

The filters were washed with 2× SSC/0.2% SDS at 65° C. until it was determined that there was minimal radioactivity coming off in the wash solution. The filters were then blotted dry and exposed to X-ray film (Kodak XAR) (Kodak, Rochester, N.Y.) with image intensifying screens at −80° C. overnight.

A total of 38 duplicating positive plaques were picked and eluted into 1 ml of SM Buffer (0.1M NaCl, 0.008M MgSO$_4$7H$_2$O, 0.05M Tris-HCl [pH7.5], 0.01 gelatin). Fifteen of the positives were then plated out (0.5 ml of a 10$^{-4}$ dilution), and used for a second round of screening, using the same hybridization/wash protocol as above. A single, well isolated hybridizing plaque was picked from each of the 15 positives and eluted into 1 ml SM solution. The phages were rescued into pBluescript (Lambda Zap II) using the ExAssist/SOLR system (Stratagene). Ampicillin resistant colonies were obtained from ten of the fifteen second round positive picks.

The subcloning process went as follows. The phagemid DNA obtained for the library screening process was labeled pSyn23/1. pSyn23/1 was double digested with the restriction enzymes EcoRI and Cla I (All restriction primers enzymes are available from Promega, Madison, Wis.) to produce a 3 kb fragment. The isolated fragment was ligated into pBluescript II (Stratagene, La Jolla, Calif.) and transformed into DH5alpha, (Stratagene) giving pSyn23/1-1. This AHAS clone was sequenced using the fmol DNA Sequencing System (Promega, Madison, Wis.) and a set of eight gene-specific primers plus the T3 sequencing primer located in the pBluescript II vector. An open reading frame of 625 amino acids was identified.

The resulting sequence of large subunit ilvG, identified as SEQ ID NO:6, had a sequence as follows:

Acetohydroxy Acid Synthase (ilvG Gene ORF)

```
>Synechocystis sp. strain PCC6803
GCCATAGGAG CCCATCGCCG ATTGAGTTCA AATTAGAAGC ACTTAGCCTA CGCTTCCTAA

ACCGATTGTC CAGTGGTTGC ATCAATTCCT AATCCCAAAA CAAATTTCCT GAAAACTGTT

CCTAGCCAAC GGCAAACCGG GGCTTATATC CTGATGGATA GCCTGAAACG CCATGGGGTC

AAACACATTT TTGGCTATCC CGGCGGGGCA ATTTTGCCCA TCTATGATGA ACTGTACCGC

TTTGAAGCGG CGGGGGAAAT TGAGCATATT TTGGTGCGCC ATGAACAAGG AGCTTCCCAT

GCGGCGGATG GGTATGCCAG AGCCACAGGT AAAGTGGGAG TTTGTTTCGG TACATCTGGA

CCAGGGGCGA CTAACTTGGT GACCGGCATT GCCAATGCCC ATTTGGACTC GGTGCCCATG

GTGGTGATTA CTGGAGAGGT GGGCCGTGCC ATGATTGGTA GCGATGCTTT CCAGGAAATT

GACATTTTTG GCATCACCTT ACCGATCGTT AAGCACTCCT ATGTGGTACG TAGTGCGGCG

GATATGGCTC GCATTGTTAC TGAGGCTTTC CATCTTGCTA GCACCGGTCG TCCCGGCCG

GTTTTGATCG ATATTCCCAA GGATGTGGGC TTAGAAGAAT GTGAGTACAT TCCCCTCGAC

CCCGGTGACG TTAATCTACC GGGTTATCGC CCCACGGTTA AAGGTAATCC CCGACAAATT

AATGCGGCAT TGCAATTGTT GGAGCAGGCC AGAAATCCCT TGCTCTACGT AGGGGGAGGG

GCGATCGCCG CCAATGCCCA TGCCCAGGTG CAGGAATTTG CGGAAAGGTT CCAGTTGCCG

GTAACAACCA CCCTGATGGG AATTGGGGCT TTTGACGAAA ACCATCCCCT TTCGGTGGGT
```

-continued
```
ATGTTGGGTA TGCATGGCCA CCGCTATGCC AACTTTGCCG TCAGCGAATG TGATTTGTTG

ATTGCAGTGG GGGCCCGTTT CGACGACCGG GTAACTGGCA AACTAGACGA ATTTGCTAGC

CGCGCCAAAG TAATTCACAT TGACATCGAC CCGGCGGAGG TGGGAAAAAA CAGGGCTCCC

GATGTGCCCA TTGTGGGGGA TGTACGCCAT GTTTTAGAAC AGCTTTTGCA GCGGGCCCGG

GAATTGGATT ACCCCACCCA TCCCCATACC ACCCAGGCAT GGTTAAATCG CATTGATCAT

TGGCGGACCG ATTACCCCCT CCAGGTGCCC CACTATGAGG ATACTATTGC CCCCCAGGAG

GTAGTACACG AAATTGGTCG CCAGGCCCCC GATGCCTACT ACACCACCGA TGTGGGACAA

CACCAAATGT GGGCGGCCCA GTTTTTGAAC AATGGCCCCC GCCGATGGAT TTCCAGTGCT

GGCTTGGGTA CGATGGGCTT TGGTTTACCT GCCGCCATGG GAGCCAAAGT GGGAGTGGGG

GACGAGCGGT CATTTGCATC AGTGGAGATG CCAGCTTCCA AATGAATCTT CAGGAACTGG

GAACCCTAGC CCAGTACGAC ATCCAGGTTA AAACTATTAT TCTCAATAAC GGTTGGCAGG

GGATGGTGCG TCAGTGGCAA CAAACTTTCT ACGAAGAACG TTATTCTGCT TCTAACATGT

CCCAGGGCAT GCCAGACATT AATCTCCTCT GTGAAGCCTA TGGCATCAAG GGTATTACTG

TGCGCAAGCG GGAAGATTTG GCCCCGGCGA TCGCCGAAAT GCTAGCCCAC AATGGTCCTG

TGGTGATGGA TGTGGTGGTC AAAAAAGATG AAAACTGTTA CCCTATGATT GCCCCCGGCA

TGAGTAATGC CCAAATGCTA GGTTTACCGG AAGTGCCGGT ACNGGACAAT GGTCCCCGGA

TGGTGGAGTG CAACCATTGC CAAACCCAAA ATTTCATCAC CCATCGTTTC TGTTCTGGTT

GTGGAGCCAA ACTCTAACCC ATAAGCCAAA ATTGAATTC
```

The predicted amino acid sequence of the open reading frame had 49% identity to the *E. coli* ilvG AHAS gene, 47% identity to the maize als2 gene, 46% identity to the *Arabidopsis* AHAS gene, and 65% identity to the sequence of the AHAS gene from the cyanobacterium *Spirulina platensis*. The high degree of sequence identity and the functional demonstration of the cyanobacterial gene fragment in complementing the AHAS deficient *E. coli* mutants strongly suggest that the fragment represents a full length cyanotacterial AHAS large subunit gene.

To confirm that these plasmids carry functional AHAS sequences, plasmid DNA from each of the ten rescued colonies was transformed into the *E. coli* strain M1262. (leuB6, ilv1614, ilvH612, λ⁻, relA1, spoT1, ilvB619, ilvG603, ilfG605(am), thi-1) (Genetics Stock Center, Yale University). This strain of *E. coli* is lacking in AHAS. Three of the plasmids were found to enable growth on M9 (+Leu) plates, thus indicating that these plasmids carried functional AHAS copies. *E. coli* M1262 expressing the cyanobacterial ahas gene were capable of growing on minimal media in the presence of OUST® sulfometuron methyl and PURSUIT® imazethapyr herbicides. The ahas gene can therefore be used for achieving herbicide tolerance in crops by transformation into the nuclear or plastidic genome.

EXAMPLE 7

Cloning and Sequencing the Large *Synechocystis* AHAS Gene

The phagemid DNA from one of the complementing lines pSyn23/I was double digested with the restriction enzymes EcoRI and ClaI (Promega) to produce a 3 kb fragment. The EcoRI and ClaI were excised out of the pBluescript phagemid as the. The isolated fragment was litigated into pBluescript and transformed into DH5alpha (Stratagene), creating pSyn23/1_I. The resulting AHAS clone was sequenced using the fmol DNA Sequencing System (Promega) and a set of eight gene-specific sequencing primers:

```
SYN1:
5' ATTGACATTT TTGGCATC 3',
identified as SEQ ID NO:7

SYN2:
5' TATCCGCCGC ACTACGTAC 3',
identified as SEQ ID NO:8

SYN3:
5' CAGGGGCGAC TAACTTGGTG AC 3',
identified as SEQ ID NO:9

SYN4:
5' ACCGCTATGC CAACTTTGCC GT 3',
identified as SEQ ID NO:10

SYN5:
5' GGAGGATAGT ACACGAAATT GG 3',
identified as SEQ ID NO:11

SYN6:
5' AAATCTTCCC GCTTGCGCAC AG 3',
identified as SEQ ID NO:12

SYN7:
5' CCAATTTCGT GTACTACCTC CTG 3',
identified as SEQ ID NO:13

SYN8:
5' AAAGTGGGAG TGGGGACGA A 3',
identified as SEQ ID NO:14
```

Additionally, a T3 sequencing primer located in the pBluescript II vector was added.

An open reading frame (ORF) of 635 amino acid was identified. The predicted amino acid sequence of the open reading frame had 49% identity of the *E. coli* ilvg AHAS gene, 47% identity to the maize als2 gene, 46% identity to the *Arabidopsis* AHAS gene, and 65% identity to the sequence of the AHAS gene from the cyanobacterium *S. plantensis*.

Cloning of the AHAS Small Subunit from *Synechocystis*

In another embodiment of the present invention, a *Synechocystis* AHAS Small Subunit nucleic acid fragment was also cloned from a genomic DNA library of cyanobacterium *Synechocystis* PCC6803.

Database searches of the complete genomic sequence of *Synechocystis* revealed three different ORFs encoding genes of acetolactate synthase, ilvG, ilvB, and ilvN. Further sequence similarity comparisons suggested that ilvN is likely to encode the small subunit of *Synechocystis* AHAS. To clone ilvN from *Synechocystis*, a PCR-based approach was adopted. Based on the sequence data, a pair of primers with the following sequences were designed, primer #1 (forward primer): 5'-cggtggaatt ttaccccaat gg-3', identified as SEQ ID NO:15 and primer #2 (reverse primer): 5'-ggc-cctaaaa cttggattcc agg-3', identified as SEQ ID NO:16 and these primers were used to PCR amplify the corresponding ORF (ilvN) from genomic DNA prepared from wild type cell cultures of *Synechocystis*.

Agarose gel analysis of PCR products yielded a band with the expected size (573 bp). PCR products have subsequently been subcloned into the invitrogen TOPO pCR2.1 TA vector.

The gene was sequenced using the same procedures as above.

The resultant *Synechocystis* sp. strain PCC6803 revealed the sequence, identified as SEQ ID NO:17:

Because the *Synechocystis* AHAS lacks the leader or transit protein sequence required to be active in the nuclear genome and transported into the chloroplast, the promoter and transit sequence of another organism was fused with the *Synechocystis* AHAS gene.

The promoter and transit sequence from the *Arabidopsis* AHAS large subunit was chosen to be fused to the *Synechocystis* AHAS large subunit gene, as there was a large degree of homology. The *Arabidopsis* genome has been sequenced and the physical and sequence information for AHAS large subunit can be found at NCBI databases hosted on the government funded NIH server, and search the "Genome Project" database for the term "*Arabidopsis*". One skilled in the art could use the information at this database to perform the cloning as follows. The final result would contain the promoter and transit sequence of the *Arabidopsis* AHAS gene, followed by the *Synechocystis* gene, followed by the *Arabidopsis* terminator. The source of the promoter and transit sequence was the construct pAC793, (which consisted of a vector and an insert with a genomic fragment containing the *Arabidopsis* AHAS promoter, transit sequence, coding region, and terminator.)

An alignment of the *Synechocystis* and *Arabidopsis* AHAS large subunits was made using the Gap program from Genetics Computer Group Inc. (GCG, Inc., Madison, Wis.). A region of homology near the N-terminal of the *Synechocystis* AHAS gene and past a putative transit sequence processing site on the *Arabidopsis* AHAS gene was chosen to make a fusion between the *Arabidopsis* transit sequence and *Synechocystis* AHAS. A common EcoRV restriction site in both the *Arabidopsis* and *Synechocystis* AHAS gene that was within a conserved region of the proteins was used as the fusion site. An AgeI restriction site occurs naturally in

```
GTGGAATTTT ACCCCAATGG CCACCGGCGA TCGCCTTCTT TGCCCCCCAT GAAACACACC

CTCTCTGTTT TAGTTGAAGA TGAAGCCGGA GTGCTAACCC GCATTGCCGG ACTATTTGCC

CGCCGTGGTT TTAACATTGA GAGCTTGGCG GTGGGGTCGG CGGAACAGGG GGACGTTTCC

CGCATCACCA TGGTGGTGCC GGGGGATGAG AACACCATCG AACAACTGAC CAAGCAACTC

TACAAGTTGG TTAACGTAAT TAAAGTACAG GACATCACCG AAACTCCCTG TGTGGAAAGG

GAATTGATGC TGGTGAAGGT GAGCGCCAAT GCCCCTAACC GAGCGGAAGT GATTGAGCTA

GCCCAGGTAT TCCGGGCCCG CATTGTGGAT ATCTCCGAAG ACACCGTCAC CATCGAATGG

TGGGGGACCC GGGTAAAATG GTAGCAATCC TCCAGATGTT GGCCAAGTTG GCATTAAAGA

GGTGGCTCGA ACGGGCAAAA TTGCTTTGGT GCGGGAATCC GGCGTCAATA CGGAATATCT

GAAATCCCTG GAATCCAAGT TTTAG
```

Construction of a Nuclear Plant Transformation Vector

Transformation of the AHAS genes into the nuclear genome required a nuclear plant transformation vector. Since branched chain amino acid biosynthesis is localized in the chloroplast in higher plants, for functional expression of AHAS in higher plants, the prokaryotic *Synechocystis* AHAS large subunit gene would need to be both expressed off of a plant expressible promoter and the protein would need to be targeted into the chloroplast. Therefore, a leader peptide will have to be fused onto the *Synechocystis* AHAS for it to be functional in the nuclear genome. When the gene is imported into the chloroplast, the leader peptide gets clipped. The final result would be the *Synechocystis* AHAS gene within the chloroplast minus the transit sequence.

the *Arabidopsis* gene. The site was found to be past the processing site and just past the stop codon of the *Arabidopsis* AHAS gene. Thus, it was chosen to create a fusion between the c-terminal end of the *Synechocystis* AHAS gene and the *Arabidopsis* AHAS termination sequence by insertion of an AgeI site in the *Synechocystis* gene in a region homologous with the *Arabidopsis* gene.

PCR primers were designed to insert an AgeI (primer SYNAGE) restriction sites on the 3-prime end of the *Synechocystis* AHAS gene. pAC793, a construct cloned from *Arabidopsis* abd contains genomic AHAS in a pGEM vector (Promega), was cut with EcoRV and AgeI to remove most of the coding sequence of the *Arabidopsis* AHAS gene from the vector. The construct pSyn23/1_I which contains a subcloned genomic fragment from *Synechocystis* (an EcoRI-ClaI subclone from the plasmid pSyn23/1. pSyn23/1 was the resulting plasmid from screening the *Synechocystis* genomic library, first paragraph of this section. Psyn23/1 was created by digesting pSyn23/1 with EcoRI and ClaI and purifying the resulting fragment. The fragment was then ligated into pBluescript II that had been previously cut with EcoRI and ClaI.) that contained the entire AHAS gene was cut with NcoI and AgeI to confirm that the correct fragment was obtained.

Using the pSYN23/1_I vector as a template a PCR reaction was carried out with the primers. The reactions gave an expected 1.9 kb PCR fragment when run out on a 0.8% TAE agarose gel. The fragment was cloned into the TA cloning vector (TA cloning kit, Invitrogen) using a Ready-To-Go ligation vial (Pharmacia). The ligation products were transformed into competent cells from the TA cloning kit (Invitrogen).

The cells were gently transferred SOC media (Qbiogene, Carlsbad, Calif.) then gently transferred to a sterile culture tube and incubated. The cells were then plated on a blue-white media and incubated overnight at 37° C. The following day white colonies were selected.

Plasmid minipreps were made from cultures of selected white colonies. Restriction digestion of the plasmids generated expected fragments on agarose gels. The construct containing the fusion of the *Arabidopsis* AHAS large subunit promoter and transit sequence, the *Synechocystis* AHAS large subunit coding region, and the *Arabidopsis* AHAS large subunit termination sequence in the pGEM vector of the pAC793 vector, was labeled pGEKI. This construct could then be used for nuclear genome transformation where the *Synechocystis* AHAS gene is to be transported from the genome into the chloroplast.

EXAMPLE 8

Creation of a Nuclear Plant Transformation Vector

A nuclear plant transformation vector was constructed as follows. PCR primers were designed to insert EcoRV (primer SYNR5) and AgeI (primer SYNAGE) restriction sites on the 5-prime and 3-prime ends, respectively, of the *Synechocystis* AHAS gene. They are identified as Sequence ID No. 18 (SYNR5) and Sequence ID No. 19 (SYNAGE). pAC793 was cut with EcoRV (just past the transit sequence) and AgeI (just past the stop codon) to remove most of the coding sequence of the Arabidopsis AHAS gene from the vector. The remaining 7 kb fragment containing the pGEM vector, the Arabidopsis AHAS promoter, the transit sequence and the termination sequence was removed from an agarose gel and treated with phenol:chloroform:isoamyl alcohol washes. The fragment was cut again with Eco RV and Age I to make sure restriction digests were complete. The construct pSyn23/1_I was obtained that contained a subcloned genomic fragment from *Synechocystis* (an Eco RI-Cla I subclone from the plasmid pSyn23/1) which in turn contained the entire AHAS gene cut with Nco I and Age I to confirm that the correct fragment was obtained.

PCR primers were designed to insert an Age I (primer SYNAGE) restriction site on 3-prime end of the *Synechocystis* AHAS gene. A 5 prime primer was designed to amplify the gene upstream of the Eco RV site.

SYNR5: 5'-GGCTGATATC CTGATGGATA GCCTG-3', identified as Sequence ID No.18

SYNAGE: 5'-TTGGCTTACC GGTTAGAGTT TGGCTC-CACA-3' identified as Sequence ID No.19.

Using the pSYN23/1_I vector as a template, a PCR reaction was carried out with the primers. The reactions (35 cycles of 94° C. melting, 55° C. annealing and 72° C. polymerase elongation (Perkin Elmer Thermocycler) gave an expected 1.9 kb PCR fragment when run out on a 0.8% TAE agarose gel.

Two μL of the PCR reaction was diluted 8x. The TA cloning vector (TA cloning kit, Invitrogen) was resuspended in 8.8 μl of TE. (Tris/EDTA, Sambrook, Fritsch, Maniatis *Molecular Cloning—A Laboratory Manual* $2^{nd}$ Ed. 1989). Two μl of TA cloning vector was added to a ligation vial (Ready-To-Go, Pharmacia). Additionally, one μL of 8× diluted PCR amplified fragment was added to the solution. Sterile water was added to bring the volume up to 20 μL. Without mixing, the vial was kept at room temperature for five minutes. After 5 minutes, the solution was mixed gently by sucking the solution in and out of a pipette tip. The sample was briefly spun to bring the solution to the bottom of the tube. The vial was then placed in a 16° C. water bath for 45 minutes.

Two μL of Beta-mercaptoethanol was added to each vial of competent cells provided in the Invitrogen TA cloning kit (Invitrogen). After 45 minutes in the ligation reaction, the vials were placed in ice for 3 minutes. Two μL of the ligation mix were added to the competent cells. The vials were then incubated on ice for 30 more minutes, followed by 60 second of heat shock at 42° C. The vials were again placed on ice for 3 minutes.

The cells were gently transferred to 450 μL of room temperature SOC media (Qbigene, Carlsbad, Calif.) then gently transferred to a sterile culture tube and incubated by an hour of shaking at 225 RPM at 37° C. The cells were then plated on LB/amp/X-gal (Sigma) (Sambrook, Fritsch, Maniatis *Molecular Cloning—A Laboratory Manual* $2^{nd}$ Ed. 1989) plates and incubated overnight at 37° C. The following day white colonies were selected.

Plasmid minipreps were made from cultures of selected white colonies. Restriction digestion of the plasmids generated expected fragments on agarose gels.

The construct containing the fusion of the *Arabidopsis* AHAS large subunit termination sequence in the pGEM vector was labeled pGEK1.

Nuclear Transformation of Cyanobacterial Genes into Plants

Agrobacterium Vector Construction

Tobacco plants were transformed with the Arabidopsis/Synechocystis AHAS fused gene. The vector pGEK1 was cut with KpnI and SalI to remove the entire AHAS fused gene from the pGEM vector and was ligated into a pBIN19 *Agrobacterium* vector (Stratagene) that was previously cut with the same enzymes. Restriction analysis indicated that the fusion gene from pGEK1 was successfully moved into the plant transformation vector.

Plants were selected on 100 mg/L kanamycin. Tobacco cultivar, Wisconsin-38 (North Carolina State University, US Tobacco Germplasm Collection) was grown aseptically on MSh⁻ medium (Sigma) containing sucrose (20 g/L) in glass (1 qt.) jars. Stem segments from plants 8-10 week were transferred to new jars for leaf propagation. Total DNA was extracted from tobacco lines using the Qiagen DNeasy Miniprep kit. (Qiagen, Inc., Valencia, Calif.).

Tests showed the transformants had little resistance to imidazolinone herbicides. This may have been due to several reasons. One reason may be that the *Synechocystis* AHAS large subunit was not accompanied by an AHAS small subunit. It has been shown that microbial AHAS genes are comprised of a large and small subunit. The large subunit of AHAS from *E. coli* does not have optimal activity in the absence of the corresponding small subunit. Since *Synechocystis*, similar to *E. coli*, is a prokaryotic organism it may share the same requirement. The absence of the small subunit may have diminished the activity of the enzyme and the ability to confer imidazolinone resistance.

Another potential reason for lack of resistance may have been the selection of the position of the fusion junction between the *Arabidopsis* AHAS transit sequence and the *Synechocystis* large subunit. An improper fusion junction may have produced a protein that either could be not localized in the chloroplast or produced a non-functional protein.

Plastid Transformation

It is believed that chloroplasts in higher plants were derived from cyanobacteria. The ancestral relationship between chloroplasts and cyanobacteria suggests that genes, gene elements, proteins, and many other features of the organisms are similar and potentially cross-functional. Cyanobacterial genes and gene elements may therefore be functional when transformed into plastid genomes. Moreover, expression of proteins from plastidic genomes obviates the need for transit sequences to traffic the protein to the proper location.

Therefore, use of cyanobacterial genes, or mutant genes isolated from resistant strains, for achieving herbicide resistance can be obtained by transformation into the plastome. Transgenes from alternative sources will confer different characteristics of the expressed traits. Regulatory elements of cyanobacterial genes can be used for control of expression in plastids. If a transgene is located in the pastime of a crop, its transfer to related species (weeds and/or crops) via pollination is prevented. The transgene will be expressed from a high number of copies per cell suggesting very high levels of expression. Furthermore, the location of transgene in the plastome obviates transport of gene products into the plastids and cyanobacterial genes can be used without modification of the coding regions.

Thus, in preferred embodiments this invention provides cyanobacteria as an alternative source of genes for plant transformations, in particular genes encoding herbicide insensitive proteins, and elements of genes for control of expression in plastids. Furthermore, since sequenced DNA fragments contain prokaryotic regulatory elements, cyanobacteria can be directly used for plastome targeted transformations.

Specifically, the *Synechocystis* AHAS large subunit gene was used for transformation into plant chloroplasts to confer herbicide resistance.

Plastidic Transformation of Cyanobacterial Genes into Plant Chloroplasts

The genes were constructed into vectors to permit incorporation into and expression in the chloroplasts. The following vectors were constructed for transformation into plastid genomes. PACBC111 and pACBC112 are related constructs differing only in the orientation of the *Synechocystis* AHAS expression cassette. These vectors were constructed as shown in FIGS. 11 and 12. The aadA sequences and the p16S expression cassette are derived from the sequences described in U.S. Pat. No. 5,877,402 (Maliga et al.). The disclosure of this patent is incorporated by reference herein in its entirety. PACBA111 is the same vector as p12delta NI. PACBC112 is the same vector as p12 delta NII. P116I (FIG. 13) is the same as pACBC222 and p116II (FIG. 14) is the same as pACBC223. pACBC111 (or p12 delta NI) and pACBC112 (or p12 delta NII) are constructs where the *Synechocystis* AHAS gene and the aadA gene are expressed from individual promoters (FIGS. 11 and 12). The p116I and p116II are discistronic constructs, one promoter expressing an operon with two genes (SynAHAS and aadA) differ from each other only in the orientation of the *Synechocystis* AHAS expression cassette (FIG. 15). The 222 and 223 vectors and the 111 and 112 vectors differ in that the p222/223 constructs are designed to express a dicistronic message while the p111/112 constructs will express the gene from a monocistronic insert.

Transformation and Regeneration of Transplastomic Plants

Plasmids pACBC222, pACBC111 and pACBC112 were used for plastid transformations. Leaves were cut and placed abaxial side down on regeneration medium (Msh⁻ medium supplemented with zeatin (2 mg/L), 1-naphthaleneacetic acid (0.1 mg/L), and sucrose (20 g/L).

Bombardments were carried out using the DuPont PDS 1000He Biolistic gun. (DuPont, Wilmington, Del.). Rupture discs (900 psi) (BioRad, Hercules, Calif.) were used, and helium pressure and vacuum levels were 1100 psi and 27" Hg, respectively.

Two days after bombardment, leaves were cut into 1 cm² pieces and placed on Spectinomycin (500 mg/L). Expanding and regeneration leaf segments were passed for up to 4 rounds on selection media. Fourth round regeneration leaf segments were passed for up to 4 rounds on selection media. Fourth round regenerates were transferred to Magenta boxes (Sigma, St. Louis, Mo.) until sufficient roots were exhibited to warrant transplantation to the greenhouse.

EXAMPLE 9

Plastid Transformation

Plasmids p116, p12delta NI and p12 delta NII were used for plastid transformations in the transformation and regeneration of transplastomic plants. Leaves were cut and placed abaxial side sown on regeneration medium (Msh⁻ medium supplemented with zeatin (2 mg/L) (Sigma), 1-naphthaleneacetic acid (0.1 mg/L), and sucrose (20 g/L). Gold was prepared for transformation by weighing 5 mg of gold (0.6 um) into Treff tubes (TreffAG, Degersheim, Switzerland) and washing once with both ETOH (100%) and sterile bidistilled water. The gold was pelleted and re-suspended in 230 uL water and mixed with 20 ug DNA (p116, p12deltaNI, or p12 delta NII), 250 uL $CaCl_2$ (2.5 M), and 50 uL spermidine (Sigma) (0.1 M free base). The gold/DNA mixture was then incubated on ice for 10 minutes and centrifuged. Two ETOH (100%) washes were performed, and the gold/DNA was suspended in 72 uL ETOH (100%). The gold suspension (5.4 ul) was applied to each macrocarrier (Bio-Rad). The macrocarriers were then placed in a dessicator for at least 1 minute.

Bombardments were carried out using the DuPont PDS 1000He Biolistic gun. Rupture disks (900 psi) were used, and helim pressure and vacuum levels were 1100 psi and 27" Hg, respectively. Two days later, leaves were cut into 1 cm² pieces and placed on selective regeneration medium containing spectinomycin (500 mg/L). Leaf segments from the first round regenerates were taken and placed on the same medium. Leaf segments were then taken from the second round regenerants and placed on two parallel selection plates. One regeneration medium contained only 500 mg/L of spectinomycin, and the other regeneration medium contained both 500 mg/L of spectinomycin and 500 mg/L of streptomycin. Leaf segments that remained green and showed signs of callus formation or regeneration on the dual selection media were selected and placed in a regeneration medium that contained only spectinomycin for a third round of regeneration. Regenerants were transferred to Magenta boxes (Sigma, St. Louse, Mo.) until sufficient roots were grown to warrant transplantation to a greenhouse.

E. Selectable Resistance Marker for Transformations

The present invention, in addition, includes the use of the cyanobacterial pds and ahas genes as a selectable marker for transformations. To test the ability of pds and ahas genes as selectable markers, aadA, a known marker for streptomycin and spectinomycin was used as a control. Upon transformation, a plant transformed with pds or ahas and aadA should show resistance to streptomycin, spectinomycin as well as the imidazolinones or 4'-fluoro-6-[(alpha,alpha,alpha,-trifluoro-m-toly)oxy]-picolinamide. In this instance, aadA, a known marker for streptomycin and spectinomycin, was used as a control. Thus, a plant grown with pds or ahas and aadA should show resistance to streptomycin, spectinomycin and imidazolinones or 4'-fluoro-6-[(alpha,alpha,alpha,-trifluoro-m-toly)oxy]-picolinamide.

To test for cyanobacterial pds and ahas's ability as selectable markers, leaf explants were transferred to medium containing both spectinomycin and streptomycin following two rounds of regeneration under spectinomycin selection. The numbers of spectinomycin/streptomycin resistant lines for each construct can be seen on Table 3.

TABLE 3

In vitro selection of plastid transformants.

| DNA Construct | # of Bombardments | # of Discrete spectinomycin-resistant lines | # of spectinomycin + streptomycin resistant lines |
|---|---|---|---|
| p12AN I | 35 | 6 | 3 |
| p12AN II | 35 | 5 | 3 |
| p116 | 90 | 12 | 1 |

Observations and photos (FIG. 8) of the PURSUIT® imazethapyr spray test were taken 5 weeks after the test was conducted. Wild type (W-38), p111, and p112 lines showed wide-spread leaf necrosis and stunting of growth when sprayed at an 18 g/ha concentration, and even more extreme effects were seen at 35 g/ha. p116 line. G-981208-1.1, showed no visible leaf damage at 18 or 35 g/ha. Growth was uninhibited at 18 g/ha, although slight stunting could be observed at 35 g/ha. PURSUIT® imazethapyr appeared to act as a strong growth regulator on the p116 line, resulting in prolific shooting and morphological abnormalities in new shoots. Leaves assumed a thin, spiny form.

Figure 9B:
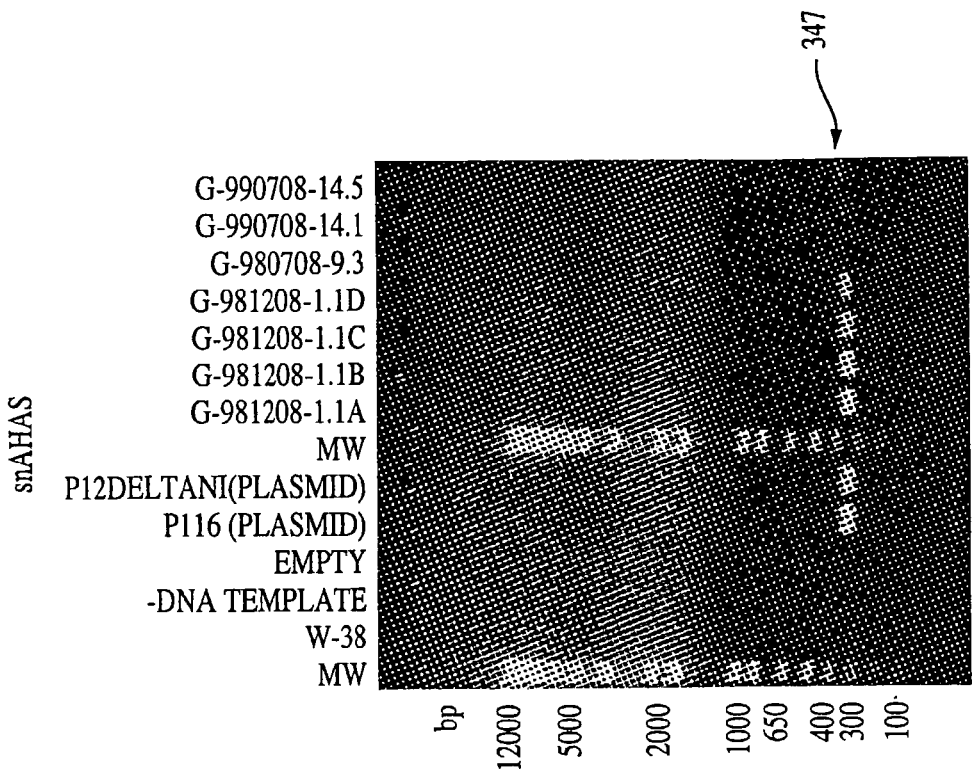
Figure 9A:
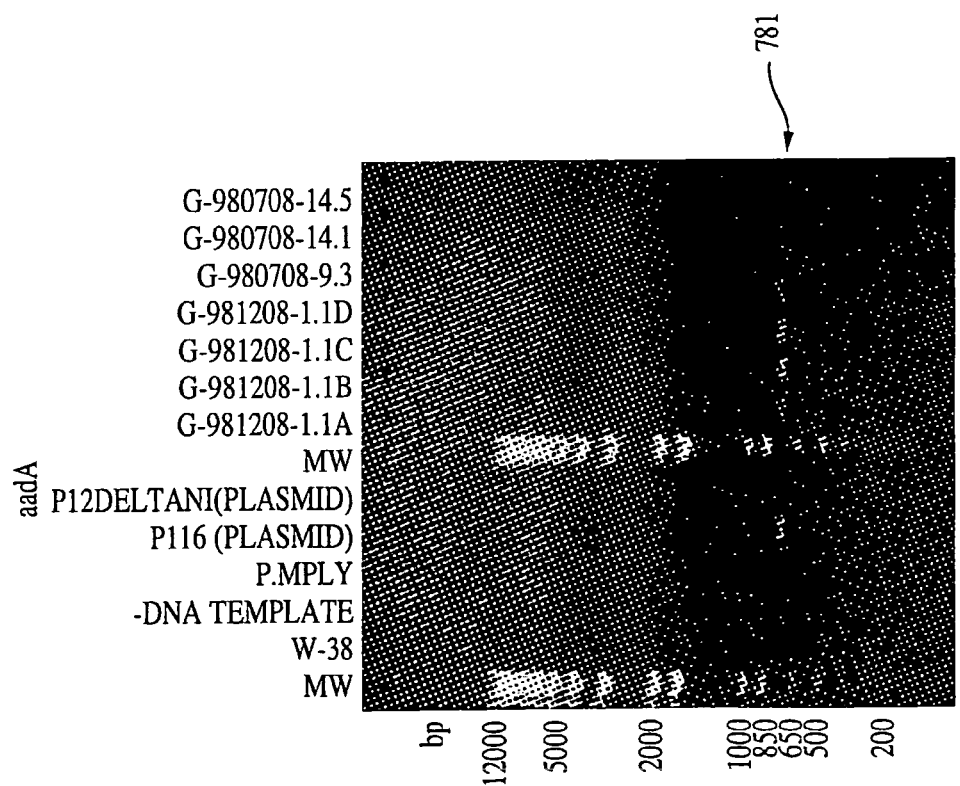

PCR amplification confirmed the integration of the Synechocystis AHAS gene into transplastomic line G-981208-1.1 (a-d) (FIGS. 9A and 9B). Clone a was sprayed at 35 g/ha PURSUIT® imazethapyr, clones b and c were sprayed at 18 g/ha, and clone d was not sprayed. The properly sized bands could be seen for the AHAS fragment.

Therefore, the ahas gene successfully integrated into the plastome and provided herbicide resistance. Because of this, cyanobacterial pds and ahas mutants can be used as a control selectable markers to test other types of transformations. The herbicide resistant pds and ahas genes can be coupled with selection on 4'-fluoro-6-[(alpha,alpha,alpha,-trifluoro-m-toly)oxy]-picolinamide or other known PDS inhibitors, and imidazolinones and other AHAS inhibiting compounds such as PURSUIT® imazethapyr for an efficient selection system for transformation. Selections can be applied to either nuclear or plastid transformation, depending on the construction of the genes.

The pACBC222 line, G-981208-1.1, tobacco cultivar, Wisconsin-38 transformed with the pACBC22 (or p116I) construct (FIG. 10) sprayed with 18 g/ha PURSUIT® imazethapyr showed about a 20% increase in AHAS enzyme resistance in the presence of PURSUIT® imazethapyr and sulfanylcarboxamides when compared with AHAS enzyme from unsprayed wild type tobacco. Interestingly enough, it appears that the snAHAS enzyme displays a level of cross resistance to both PURSUIT® imazethapyr and sulfanylcarboxamides, although they are both quite dissimilar structurally.

F. Cells, Tissue, Plants Derived from Chloroplast-Mediated Transformations

A further objective of this invention provides for cells, tissues, plants, pollen derived from said transformation of the mutant Synechocystis pds gene and the ahas genes into untransformed plant cell, using. Alternatively, mutant forms of pds genes with mutation(s) at position(s) similar to the Synechocystis gene can be obtained for any given crop species, and used further for genetic transformation. Synechocystis mutant pds gene(s) resistant to 4'-fluoro-6-[(alpha,alpha,alpha,-trifluoro-m-toly)oxy]-picolinamide and the mutant AHAS gene comprising the ahas small subunit and the ahas large subunit identified in these processes can be, respectively, introduced directly into crops for engineering 4'-fluoro-6-[(alpha,alpha,alpha,-trifluoro-m-toly)oxy]-picolinamide resistance via chloroplast-mediated transformation and imidazolinone resistance. The genes can also be used for generating resistance to other pds or AHAS inhibiting herbicides.

While the preferred embodiments of the invention has been illustrated and described, it will be appreciated that various changes can be made therein without departing from the spirit and scope of the invention.

REFERENCES

Patents

| WO 9,628,014 | Hirschberg et al | 1996 |
| WO 9,806,862 | Calgene | 1997 |
| WO 9,820,144 | Zeneca | 1998 |
| JP 6,343,473 | Kirin Brewery | 1994 |
| U.S. Pat. No. 5,378,824 | Dupont | 1995 |
| U.S. Pat. No. 5,661,017 | Dunahay et al | 1995 |

Other References

Babczinski, P., Sandmann, G., Schmidt, R., Shiokawa, Kozo, Yasui, Katzucsmi, Pestic. Biochem. Physiol., 1995, 52, 1, p 33-44

Boger, P. Sandmann, G., Pesticide Outlook, 1998, 9, 6, p. 29-35

Chamowitz, D. Sandmann, G. Hirschberg, J., J. Biol. Chem., 1993, 268, 23, p. 17348-53

Chamovitz, D., Pecker, I., Hirschberg, J., Plant Molecular Biology, 16, pp. 967-974 (1991)

Clarke, I. E. Sandmann, G. Brawley, P. M. Boeger, P., Pestic. Biochem. Physiol., 1985, 23, 3, p. 335-340

Duggleby et al, Gene, 1997, 190, p. 245

Dzelzkalns & Bogorad, 1998, *The EMBO Journal*, 7, p. 333-338

Freiberg, D. Seijffers, J., Z Naturforsch, 1990, C, 45, 5, P. 538-543

Kowalczyl-Schroder, S. Sandmann, G., Pestic. Biochem. Physiol., 1992, 42, 1, p. 7-12

Hattori et al, Mol. & Gen. Genet., 1995, 246, p. 419-425

Linden, H., Sandmann, G., Chamovitz, D., Hirschberg, J., Booger, P. Pesticide Biochemistry and Physiology, 35, pp. 46-51 (1990)

Martinez-Ferez, I., Vioque, A., Plant Molecular Biology, 18, pp. 981-983, (1992)

Mifflin, B. J., Arch. Biochm. Biophys., 1971, 146, p. 542-550

Powell, H. A. Kerley, N. W. Powell, P., Br. Phycol. J., 1990, 25 1, p. 93

Sandmann, G. Schmidt A. Linden, H. Boger, P., Weed Science, 39, pp. 474-479 (1991)

Sandmann, G. Schneider, C. Boger, P., Z Naturforsch 1996, 51, 7-8, p. 534-538

Sandmann, G. Fraser, P. D., Z Naturforsch 1993, C, 48, 3-4, p. 307-311

Sandmann, G. Schneider, C. Boger, P., Z Naturforsch 1996, 51, 7-8, p. 534-538

Sandmann, G. Fraser, P. D. Linden, H., Res. Photosynth. Proc. Int. Congr., 1992, 3, p. 51-4

Sandmann, G. Kowalezyl-Schroder, S. Taylor, H. M. Boeger, P., Pestic. Biochem. Physiol., 1992, 42, 1, p. 1-6

Sandmann, G., Target Assays Mod. Herbic. Relat. Phytotoxic Compd., 1993, p. 15-20

Sandmann, G., Chamovitz, D., Hirchberg, J., The Journal of Biological Chemistry, Vol. 268, No. 23, pp. 17348-17353 (1993)

Singh B K, Stidham M A, Shaner D L, Anal. Biochem., 1998, 171:173-179

Singh B K, Stidham M A, Shaner D L, J. Chromatography, 1998, 444, 251

Weinstock et al., J. Bacteriol., 1992, 174, p. 5560-5566

Williams et al., 1998, Methods in Enzymology, 167, p. 766-778

Windhoevel, U. Geiges, B. Sandman, G. Boeger, P., Pestic. Biochem. Physiol., 1994, 49, 1, p. 63-71

Windhoevel, U. Sandman, G. Boeger, P. Pestic. Biochem. Physiol., 1997, 57, 1, p. 68-78

Windhoevel, U., Geiges, B. Sandman, G. Goeger, P., Plant Physiol., 1994, 104, 1, p. 6371 Methods in Enzymology, 167, 703-712

We claim:

1. An isolated polynucleotide comprising nucleotides 1 to 1735 of SEQ ID NO:3.
2. A replicable expression vector comprising the polynucleotide of claim 1.
3. A transgenic plant transformed with the replicable expression vector of claim 2.
4. The transgenic plant of claim 3, wherein the transgenic plant exhibits resistance to herbicides selected from the group consisting of 4'-fluoro-6-[(alpha,alpha,alpha,-trifluoro-m-tolyl)oxy]-picolinamide, (2E)-2-[amino(benzylsulfany)methylene]-1-(2,4-dichlorophenyl)-1,3-butanedione, pyridine, 2-[(3,3-dichloro-2-propenyl)oxy]-4-methyl-6-[[2-(trifluoromethyl)-4-pyrodinyl]oxy] and 1,2,4,5-benzenetetracarboxamide, N,N',N'',N'''-tetrakis[5-(benzoylamino)-9,10-dihydro-9,10-dioxo-1-anthracenyl.
5. The transgenic plant of claim 3, wherein the transgenic plant exhibits resistance to 4'-fluoro-6-[(alpha,alpha,alpha,-trifluoro-m-tolyl)oxy]-picolinamide.
6. A progeny derived from the transgenic plant of claim 3.
7. A selectable marker for transformation comprising the polynucleotide of claim 1.

* * * * *

SEQUENCE LISTING

```
<160> NUMBER OF SEQ ID NOS: 19

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 1
cgaattccct ggtagcattt aatacaaatt ggc                                33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 2
cgcataagct ttgcagatgg agacggtttg ggc                                33

<210> SEQ ID NO 3
<211> LENGTH: 1735
<212> TYPE: DNA
<213> ORGANISM: Synechocystis sp.

<400> SEQUENCE: 3
ccctggtagc atttaataca aattggctat cttggcaaag tcccccgaaa tattacgaaa      60
cgtaaagtat aataacaatc aacctgtaaa ccccaaatgc cttagcgaga cagtaaccca     120
tgcgcgttgt gatcgccgga gccggattag ccggcctagc ctgtgccaaa tacttagccg     180
atgcgggctt taccccgtc gtcttggaac gtagggatgt attaggcggg aagatcgccg      240
cgtggaaaga tgaggacgga gattggtacg aaaccggcct acacattttt tttgggggcct    300 atcccaacat gttgcagtta tttaaggaat tggatatcga agatcgtctg caatggaaag     360
```

```
agcacagcat gatcttcaac caaccagaga aaccaggtac ctactctcgg ttcgattttc      420
cggatattcc ggcccccatc aatggtttgg tagccattct tcgcaacaac gatatgctta      480
cctggccgga gaaaattcgc tttggcttgg gactcttgcc ggccattgtc cagggccaga      540
gctatgtgga agaaatggat aaatacactt ggtcagagtg gatggccaaa caaaatattc      600
ccccccgcat cgaaaagaa gttttcattg ccatgagtaa gacgttgaac tttattgatc       660
ccgatgaaat ttccgccacc attttactta ctgccctcaa tcgcttttta caggaaaaaa      720
atggctctaa gatggcattc ctggatgggg caccaccgga gcgtctttgc caacctttgg      780
tcgactatat tacggaacgg ggagggggaag tacacattaa taaacctctc aaagaaattt     840
tgcttaatga agatggttcc gttaagggtt acttaatccg gggcctagat ggagcccccg      900
acgaagtgat cacagcggat ttatatgtgt ctgccatgcc ggtggatccc ctgaaaacca     960
tggtgccagc gccctggaga gaatatcctg agtttaagca aatccaaggt ttggaaggag     1020
tcccggtcat taacctccac ctgtggtttg accgtaagtt aaccgacatt gatcatttgt     1080
tattctcccg atcgccgttg ttgagtgttt acgccgacat gagcaacacc tgccgagaat     1140
acagtgatcc agacaaatcc atgttggaat tggtgctggc tccggcccag gattggatcg     1200
gcaaatccga cgaagagatt gtggcggcca ccatggcgga gatcaagcaa ctctttcccc     1260
aacacttcaa cggggataat ccagcccgac tgcttaaatc ccacgtggtc aaaaccccc     1320 gctcagtcta caaagctacc cccggaaggc aggcttgtcg ccccgatcaa cggacatcgg     1380
tgcccaactt ttacctagca ggggacttca ccatgcaaaa atacttgggc agtatggaag     1440
gggcggtgct ttccggcaaa caatgcgccc aggcgatcgc cgccgatttc aaccccccaaa    1500 ccgttccccc caccagggaa atagtcaccg tgggttaagc cgcctggact ccctggtaat     1560
cttcctgaca aatggcaacc ctaatgcgac aatgctaaat ggctaacggt caaatttctc      1620
cccagcgtgc agttaccaaa ccccaatcct ggtggctgac ttccgaaccc cgtccgtcct     1680
taatgttaca actgcccaaa ccgtctccat ctgcaaagcc ctgtgcttct gttga           1735
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (3)
<223> OTHER INFORMATION: A, G, C or T
<220> FEATURE:
<221> NAME/KEY: modified_base
<222> LOCATION: (6)
<223> OTHER INFORMATION: A, G, C or T
<220> FEATURE:
<221> NAME/KEY: modified_base
<222> LOCATION: (12)
<223> OTHER INFORMATION: G, A, C or T

<400> SEQUENCE: 4
ggnacngayg cnttycarga                                                    20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer
<220> FEATURE:

<221> NAME/KEY: modified_base
<222> LOCATION: (10)
<223> OTHER INFORMATION: A, G, C or T
<220> FEATURE:
<221> NAME/KEY: modified_base
<222> LOCATION: (13)
<223> OTHER INFORMATION: A, G, C or T

<400> SEQUENCE: 5
ytsccaytgn cknaccat                                               18

<210> SEQ ID NO 6
<211> LENGTH: 1959
<212> TYPE: DNA
<213> ORGANISM: Synechocystis sp.
<220> FEATURE:
<221> NAME/KEY: modified_base
<222> LOCATION: (1843)
<223> OTHER INFORMATION: a, t, c, g, other or unknown

<400> SEQUENCE: 6

```
gccataggag cccatcgccg attgagttca aattagaagc acttagccta cgcttcctaa     60
accgattgtc cagtggttgc atcaattcct aatcccaaaa caaatttcct gaaaactgtt    120
cctagccaac ggcaaaccgg ggcttatatc ctgatggata gcctgaaacg ccatggggtc    180
aaacacattt ttggctatcc cggcggggca atttttgccca tctatgatga actgtaccgc    240
tttgaagcgg cggggggaaat tgagcatatt ttggtgcgcc atgaacaagg agcttcccat    300
gcggcggatg gtatgccag agccacaggt aaagtgggag tttgtttcgg tacatctgga     360
ccagggcga ctaacttggt gaccggcatt gccaatgccc atttggactc ggtgcccatg     420
gtggtgatta ctggagaggt gggccgtgcc atgattggta gcgatgcttt ccaggaaatt    480
gacatttttg gcatcacctt accgatcgtt aagcactcct atgtggtacg tagtgcggcg    540
gatatggctc gcattgttac tgaggctttc atcttgcta gcaccggtcg tcccgggccg     600
gttttgatcg atattcccaa ggatgtgggc ttagaagaat gtgagtacat tcccctcgac    660
cccggtgacg ttaatctacc gggttatcgc cccacggtta aggtaatcc ccgacaaatt     720
aatgcggcat tgcaattgtt ggagcaggcc agaaatccct tgctctacgt aggggggaggg  780
gcgatcgccg ccaatgccca tgcccaggtg caggaatttg cggaaaggtt ccagttgccg    840
gtaacaacca ccctgatggg aattgggggt tttgacgaaa accatcccct ttcggtgggt    900
atgtttgggta tgcatggcca ccgctatgcc aactttgccg tcagcgaatg tgatttgttg    960
attgcagtgg gggcccgttt cgacgaccgg gtaactggca aactagacga atttgctagc  1020
cgcgccaaag taattcacat tgacatcgac ccggcggagg tgggaaaaaa cagggctccc   1080
gatgtgccca ttgtggggga tgtacgccat gttttagaac agcttttgca gcgggcccgg   1140
gaattggatt accccaccca tccccatacc acccaggcat ggttaaatcg cattgatcat   1200
tggcggaccg attaccccct ccaggtgccc cactatgagg atactattgc cccccaggag   1260
gtagtacacg aaattggtcg ccaggccccc gatgcctact acaccaccga tgtgggacaa   1320
caccaaaatgt gggcggccca gttttttgaac aatggccccc gccgatggat ttccagtgct   1380
ggcttgggta cgatgggctt tggttaacct gccgccatgg gagccaaagt gggagtgggg   1440
gacgagcggt catttgcatc agtggagatg ccagcttcca aatgaatctt caggaactgg   1500
gaaccctagc ccagtacgac atccaggtta aaactattat tctcaataac ggttggcagg   1560
ggatggtgcg tcagtggcaa caaactttct acgaagaacg ttattctgct tctaacatgt   1620
cccagggcat gccagacatt aatctcctct gtgaagccta tggcatcaag ggtattactg   1680
```

```
tgcgcaagcg ggaagatttg gccccggcga tcgccgaaat gctagcccac aatggtcctg   1740
tggtgatgga tgtggtggtc aaaaaagatg aaaactgtta ccctatgatt gccccggca    1800 tgagtaatgc ccaaatgcta ggtttaccgg aagtgccggt acnggacaat ggtccccgga   1860
tggtggagtg caaccattgc caaacccaaa atttcatcac ccatcgtttc tgttctggtt   1920
gtggagccaa actctaaccc ataagccaaa attgaattc                          1959
```

```
<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 7
attgacattt ttggcatc                                                 18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 8
tatccgccgc actacgtac                                                19

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 9
caggggcgac taacttggtg ac                                            22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
accgctatgc caactttgcc gt                                            22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
ggaggatagt acacgaaatt gg                                            22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer
```

```
<400> SEQUENCE: 12
aaatcttccc gcttgcgcac ag                                                22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 13
ccaatttcgt gtactacctc ctg                                               23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 14
aaagtgggag tgggggacga a                                                 21

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 15
cggtggaatt ttaccccaat gg                                                22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 16
ggccctaaaa cttggattcc agg                                               23

<210> SEQ ID NO 17
<211> LENGTH: 565
<212> TYPE: DNA
<213> ORGANISM: Synechocystis sp.

<400> SEQUENCE: 17
gtggaatttt accccaatgg ccaccggcga tcgccttctt tgcccccat gaaacacacc         60 ctctctgttt tagttgaaga tgaagccgga gtgctaaccc gcattgccgg actatttgcc       120
cgccgtggtt ttaacattga gacttggcg gtggggtcgg cggaacaggg ggacgtttcc        180
cgcatcacca tggtggtgcc gggggatgag aacaccatcg aacaactgac caagcaactc      240
tacaagttgg ttaacgtaat taaagtacag gacatcaccg aaactccctg tgtggaaagg      300
gaattgatgc tggtgaaggt gagcgccaat gcccctaacc gagcggaagt gattgagcta      360
gcccaggtat tccgggcccg cattgtggat atctccgaag acaccgtcac catcgaatgg      420
tgggggaccc gggtaaaatg gtagcaatcc tccagatgtt ggccaagttg gcattaaaga      480
ggtggctcga acgggcaaaa ttgctttggt gcgggaatcc ggcgtcaata cggaatatct      540
gaaatccctg gaatccaagt tttag                                            565
```

```
<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 18
ggctgatatc ctgatggata gcctg                                              25

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 19
ttggcttacc ggttagagtt tggctccaca                                         30
```